(12) United States Patent
Heinks et al.

(10) Patent No.: US 7,474,247 B1
(45) Date of Patent: Jan. 6, 2009

(54) DETECTING OVERLOADING OF AN ANALOG-TO-DIGITAL CONVERTER OF AN IMPLANTABLE MEDICAL DEVICE

(75) Inventors: Michael W. Heinks, New Brighton, MN (US); Joel A. Anderson, Brooklyn Park, MN (US); Wenxiao Tan, Murphy, TX (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 11/861,945

(22) Filed: Sep. 26, 2007

(51) Int. Cl.
H03M 1/12 (2006.01)
(52) U.S. Cl. ..................... 341/155; 341/143
(58) Field of Classification Search .......... 341/143, 341/155
See application file for complete search history.

(56) References Cited

U.S. PATENT DOCUMENTS

| | | | |
|---|---|---|---|
| 4,990,914 A | 2/1991 | Giancarlo | |
| 5,208,597 A | 5/1993 | Early et al. | |
| 5,329,281 A | 7/1994 | Baumgartner et al. | |
| 5,606,320 A | 2/1997 | Kleks | |
| 5,742,246 A * | 4/1998 | Kuo et al. ............ | 341/143 |
| 6,064,326 A | 5/2000 | Krone et al. | |
| 6,100,834 A | 8/2000 | Lewyn | |
| 6,354,299 B1 * | 3/2002 | Fischell et al. ......... | 128/899 |
| 6,362,763 B1 | 3/2002 | Wang | |
| 6,389,315 B1 * | 5/2002 | Schu et al. ............ | 607/16 |
| 6,535,153 B1 | 3/2003 | Zierhofer | |
| 6,556,859 B1 * | 4/2003 | Wohlgemuth et al. .... | 600/509 |
| 6,567,025 B2 | 5/2003 | Schreier et al. | |
| 6,700,520 B1 | 3/2004 | Miller | |
| 6,924,760 B1 | 8/2005 | McLeod et al. | |
| 7,015,853 B1 | 3/2006 | Wolff et al. | |
| 7,049,990 B2 | 5/2006 | Ranganathan | |
| 7,053,807 B1 | 5/2006 | Gaalaas | |
| 7,079,061 B2 | 7/2006 | Schuurmans | |
| 7,102,558 B2 | 9/2006 | Deval | |
| 7,142,143 B2 | 11/2006 | Draxelmayr | |
| 7,176,817 B2 | 2/2007 | Jensen | |
| 7,221,303 B1 | 5/2007 | Melanson | |

(Continued)

OTHER PUBLICATIONS

U.S. Appl. No. 11/861,856, filed Sep. 26, 2007 entitled "Capacitive Digital-to-Analog Converter Reset in an Implantable Medical Device Analog-to-Digital Converter" reference No. P0028398.00.

(Continued)

*Primary Examiner*—Khai M Nguyen
(74) *Attorney, Agent, or Firm*—Michael C. Soldner

(57) ABSTRACT

In general, this disclosure is related to detecting overload within an analog-to-digital converter (ADC) of an implantable medical device (IMD). The IMD may include an overload detection module that determines whether the ADC is operating in an overload condition. When the overload detection module determines the ADC is operating in the overload condition for a particular period of time, the ADC may send an overload signal to a processor that processes the output of the ADC. The overload signal notifies the processor that the ADC is operating in or is close to operating in the overload condition. In response to the indication from the ADC, the processor of the IMD may disregard the output of the ADC. The processor may continue to disregard the output of the ADC until the overload signal is deactivated, thereby indicating that the ADC is no longer in an overloaded condition.

25 Claims, 17 Drawing Sheets

U.S. PATENT DOCUMENTS

| | | |
|---|---|---|
| 7,245,246 B2 | 7/2007 | Ihs et al. |
| 7,345,607 B1 * | 3/2008 | Frigaard et al. ............. 341/143 |
| 2005/0162222 A1 | 7/2005 | Hezar et al. |
| 2007/0032734 A1 | 2/2007 | Najafi et al. |
| 2007/0208262 A1 * | 9/2007 | Kovacs ....................... 600/509 |

OTHER PUBLICATIONS

U.S. Appl. No. 11/861,920, filed Sep. 26, 2007 entitled "Implantable Medical Device With Low Power Delta-Sigma Analog-to-Digital Converter" reference No. P0028368.00.

* cited by examiner

DETECTING OVERLOADING OF AN ANALOG-TO-DIGITAL CONVERTER OF AN IMPLANTABLE MEDICAL DEVICE

TECHNICAL FIELD

This disclosure relates to implantable medical devices and, more particularly, analog-to-digital conversion in implantable medical devices.

BACKGROUND

In a variety of applications, implantable medical devices are used for one or both of monitoring or delivering therapy to a patient. For example, cardiac pacemakers typically monitor electrical signals from the heart, i.e., an electrocardiogram (ECG), and deliver electrical stimulation to the heart, via electrodes. The electrodes may be positioned within the heart, and coupled to the pacemaker by intravenous leads, or may be positioned subcutaneously using any non-intravenous location, such as below the muscle layer or within the thoracic cavity, for example.

In the case of demand pacing, for example, a cardiac pacemaker monitors the ECG to determine whether an intrinsic cardiac depolarization, e.g., a P-wave or R wave, occurs within a rate interval. If an intrinsic depolarization occurs, the pacemaker resets a timer and continues to monitor the electrical signals from the heart. If an intrinsic depolarization does not occur, the pacemaker delivers one or more electrical pulses to the heart, and resets the timer.

As another example, an implantable medical device may monitor electrical signals within the brain, e.g., an electroencephalogram (EEG), sensed via electrodes. An implantable medical device may monitor the EEG to, for example, identify epileptic seizures, or other neurological issues. In some cases an implantable medical device may deliver electrical stimulation to the brain, or other tissue within the patient, in response to or based on the analysis of the EEG. In other examples, implantable medical devices may monitor any of a variety of signals generated by any of a variety of sensors based on physiological parameters of a patient, such as pressure, impedance, temperature, or physical motion.

Historically, implantable medical devices have used analog circuitry to process or analyze such physiological signals. For example, many pacemakers have used analog circuitry to process the ECG, e.g., to detect P-waves and R-waves. More recently, use of digital signal processing for this purpose has been considered or implemented.

Digital signal processing requires conversion of the analog signal, e.g., ECG, to a digital signal using an analog-to-digital converter (ADC). One type of ADC is a delta-sigma ADC. A delta-sigma ADC tracks the changes in the analog input signal by comparing the input signal to a feedback signal.

In general, based on its complexity and sampling rate, there is a limit to the magnitude and rate of change of an input signal that a delta-sigma ADC can track. Implantable medical devices can be exposed to electro-magnetic interference (EMI) that can induce large voltages on the leads or sensor inputs. In the presence of EMI, a delta-sigma ADC can be overloaded so that incorrect data streams are generated, which may be incorrectly interpreted by a system that analyzes the output digital signal. For example, a cardiac pacemaker may incorrectly interpret low frequency shifts in the output digital signal caused by EMI to be intrinsic cardiac activity. In this case, a pacemaker operating in a demand mode may incorrectly inhibit delivery of pacing pulses in the presence of EMI.

SUMMARY

In general, this disclosure is related to detecting overload within an analog-to-digital converter (ADC) of an implantable medical device (IMD). The IMD may be exposed to non-physiological signals, such as electro-magnetic interference (EMI), which can induce large voltages on one or more of electrodes. In the presence of these large voltages, and ADC of IMD may become overloaded, thereby causing the ADC to output data that includes errors. The IMD may analyze the incorrect data, and erroneously interpret the data as indicating a condition that does not exist, or fail to indicate a condition that does exist. This may cause the IMD to incorrectly apply or disable therapy.

To avoid these situations, an IMD according to the invention may include an overload detection module that determines whether the ADC is operating in an overload condition due to large voltages. When the overload detection module determines the ADC is operating in the overload condition for a particular period of time, the overload detection module may send an overload signal to a processor that receives the output of the ADC. The overload signal notifies the processor that the ADC is operating in or is close to operating in the overload condition. In response to the indication from the ADC, the processor of the IMD may disregard the output of the ADC. The processor may continue to disregard the output of the ADC until the overload signal is deactivated, thereby indicating that the ADC is no longer in an overloaded condition.

Alternatively, or additionally, the IMD may include an overload prediction module that detects when the ADC is approaching an overload condition. In response to the detection, the ADC may either output a warning signal to the processor and/or adjust the operation of the ADC in response to the prediction. The ADC may, for example, be reprogrammed from a normal counting mode that counts by +/−1 to a high slew count mode that counts by +/−2. Alternatively, or additionally, the ADC may be clocked at an increased clock rate to operate in a high slew mode. In this manner, the ADC may accommodate for the detected conditions to better track the inputs.

In one embodiment, a method comprises converting an analog input signal from a sensor into a digital signal with an analog-to-digital converter (ADC) of an implantable medical device, determining that the ADC is in an overload condition based on at least one signal from the ADC and disregarding the digital signal by a processor of the implantable medical device in response to the determination.

In another embodiment, an implantable medical device comprises an analog-to-digital converter (ADC) that converts an analog input signal from a sensor into a digital signal, an overload detection module that determines that the ADC is in an overload condition based on at least one signal from the ADC and a processor that disregards the digital signal in response to the determination.

In another embodiment, an implantable medical device comprises an analog-to-digital converter (ADC) that converts an analog input signal from a sensor into a digital signal, wherein the ADC includes a clamping integrator that generates a clamp signal when the clamping integrator is operating in a clamped mode, an overload detection module that determines that the ADC is in an overload condition based on the clamp signal from the ADC, and a processor that disregards the digital signal in response to the determination.

In another embodiment, an implantable medical device comprises an analog-to-digital converter (ADC) that converts an analog input signal from a sensor into a digital signal, an overload detection module that that generates a low toggle signal if a quantizer of the ADC outputs the same value during a threshold number of consecutive clock cycles and determines that the ADC is in an overload condition based on the low toggle and a processor that disregards the digital signal in response to the determination.

In another embodiment, an implantable medical device comprises means converting an analog input signal from a sensor into a digital signal, means for determining that the converting means is operating in an overload condition based on at least one signal from the converting means and means for disregarding the digital signal of the implantable medical device in response to the determination.

In another embodiment, an implantable medical device comprises an analog-to-digital converter (ADC) that converts an analog input signal from a sensor into a digital signal and an overload prediction module that determines that the ADC is approaching an overload condition based on at least one signal from the ADC, and generates a warning signal in response to the determination. The ADC switches from a normal slew operating mode to a high slew operating mode in response to the warning signal.

The details of one or more embodiments are set forth in the accompanying drawings and the description below. Other features, objects, and advantages of the techniques of this disclosure will be apparent from the description and drawings, and from the claims.

DETAILED DESCRIPTION

Figure 1:
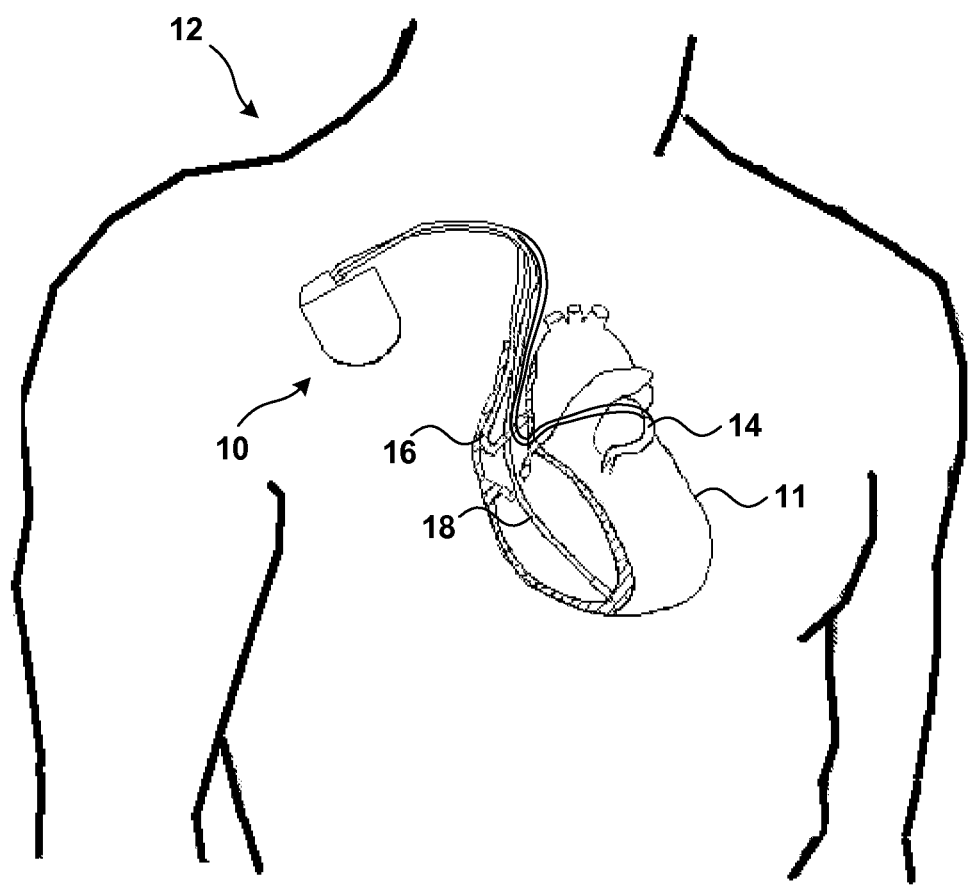
FIG. 1 is a conceptual diagram illustrating an implantable medical device ("IMD") implanted within a patient.

FIG. 1 is a conceptual diagram illustrating an implantable medical device ("IMD") 10 implanted within a patient 12. IMD 10 is implanted near a heart 11 of patient 12. Patient 12 ordinarily will be a human patient. In some cases, however, IMD 10 may be used within non-human patients. IMD 10 includes leads 14, 16 and 18 that extend from IMD 10 to heart 11 of patient 12. In the example illustrated in FIG. 1, leads 16 and 18 extend from IMD 10 to the right atrium and ventricle, respectively, of heart 11. Lead 14 extends from IMD 10 into the coronary sinus of heart 11, proximate to the left ventricle of the heart. Although the example IMD 10 illustrated FIG. 1 includes three leads, IMD 10 may be coupled to any number of leads that are located within or near heart 11.

Leads 14, 16 and 18 include one or more electrodes that may be used for sensing one or more parameters of heart 11 and/or delivering therapy to heart 11. The electrodes may, for example, sense one or more electrical signals attendant to the depolarization and repolarization of the heart 11, e.g., an electrocardiogram (ECG), and leads 14, 16 and 18 may convey the sensed signals to IMD 10. IMD 10 may also deliver therapy, e.g., in the form of one or more pulses, to heart 11 via leads 14, 16 and/or 18.

In the illustrated example, IMD 10 is an implantable pacemaker-cardioverter-defibrillator (PCD) that provides pacing pulses for causing depolarization of cardiac tissue via one or more electrodes on leads 14, 16 and/or 18. IMD 10 may operate in a demand pacing mode, in which IMD 10 delivers pacing pulses based on the absence of an intrinsic depolarization in the ECG. As a PCD, IMD 10 also provides cardioversion or defibrillation pulses, or high-rate tachyarrhythmia pacing pulses, for treating cardiac arrhythmias, atrial fibrillation, ventricular fibrillation or tachyarrhythmia via one or more electrodes on leads 14, 16 and/or 18. In such embodiments, IMD 10 analyzes the ECG to identify the cardiac arrhythmias, e.g., based on heart rate and/or ECG morphology. In other embodiments, IMD 10 may be an implantable pacemaker that does not provide cardioversion or defibrillation pulses, or high-rate tachyarrhythmia pacing pulses, for treating cardiac arrhythmias, atrial fibrillation, ventricular fibrillation or tachyarrhythmia, or an implantable cardioverter-defibrillator (ICD) that does not provide pacing pulses for causing depolarization of cardiac tissue.

The IMD 10 illustrated in FIG. 1 is an example of the type of device in which various techniques described in this disclosure may be embodied, and is not to be considered as limiting of the scope of the techniques as claimed. The techniques described herein may be practiced in a wide variety of medical device implementations. Additional example applications of the various techniques described herein with reference to cardiac pacemaker IMD 10 are discussed below.

Figure 2:
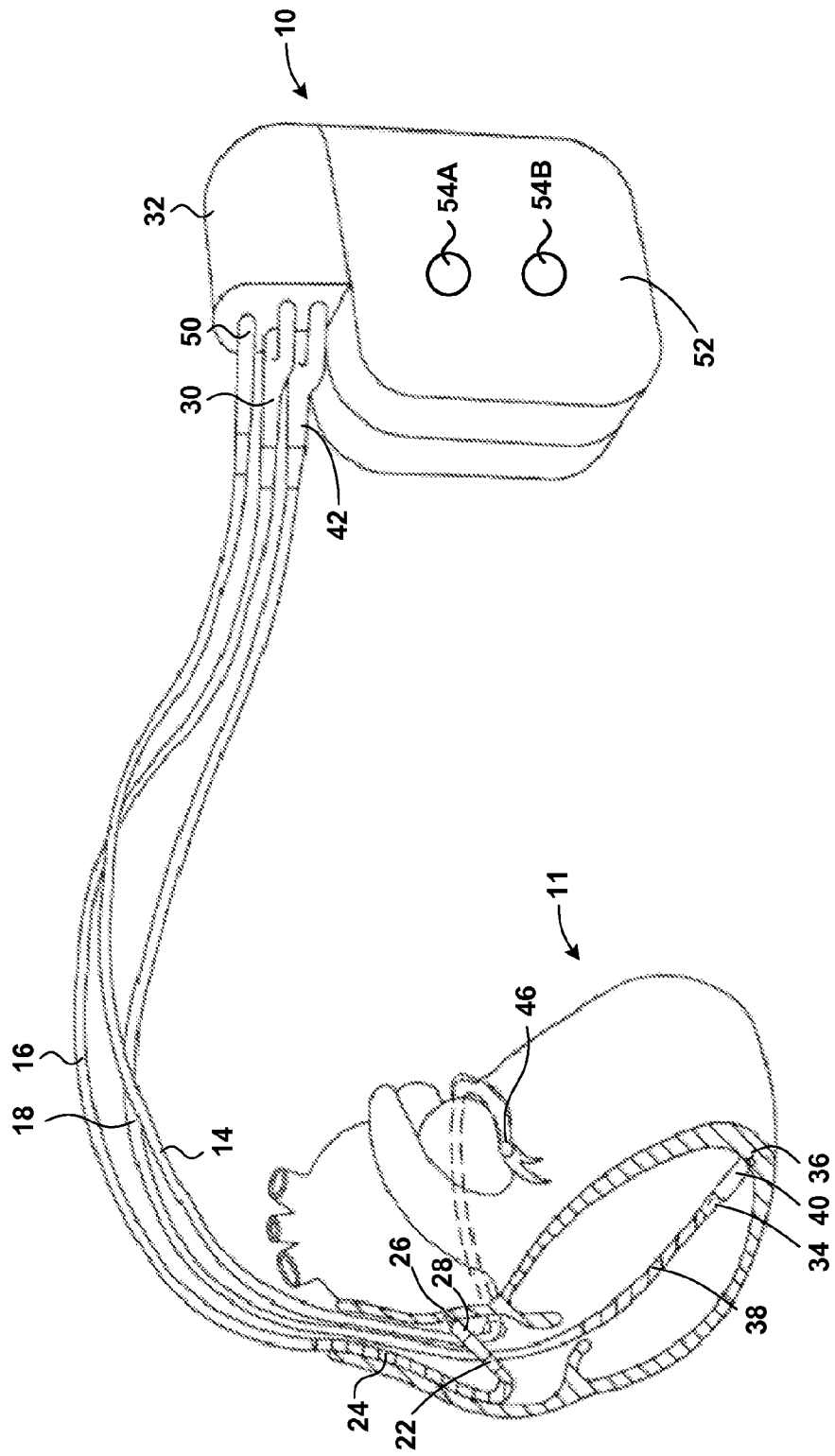
FIG. 2 is a conceptual diagram illustrating the IMD in conjunction with a heart, in further detail.

FIG. 2 is a conceptual diagram illustrating IMD 10 in conjunction with human or mammalian heart 11, and in further detail. The specific structure of IMD 10 is described below for purposes of example, and should not be considered limiting of the techniques as claimed.

As shown in FIG. 2, IMD 10 may include an atrial lead 16, which may include an elongated insulative lead body carrying three concentric coiled conductors, separated from one another by tubular insulative sheaths. Located adjacent the J-shaped distal end of atrial lead 16 is a ring electrode 22, an elongated coiled electrode 24, and an extendable helix electrode 26 mounted retractably within an insulative electrode head 28. Each of electrodes 22, 24 and 26 is coupled to one of the coiled conductors within the body of lead 16. Electrodes 22, 24 and 26 are employed for atrial pacing and for sensing atrial depolarizations, often referred to as atrial events or P-waves. At the proximal end of atrial lead 16 is a bifurcated connector 30 that is inserted into a connector block 32 associated with IMD 10. In particular, bifurcated connector 30 carries three electrical connectors, each coupled to one of the coiled conductors.

IMD 10 may also include a ventricular lead 18 having an elongated insulative lead body carrying three concentric coiled conductors, separated from one another by tubular insulative sheaths. Located adjacent the distal end of ventricular lead 18 are a ring electrode 34, an extendable helix electrode 36 mounted retractably within an insulative electrode head 40 and an elongated coil electrode 38. Each of electrodes 34, 36 and 38 is coupled to one of the coiled conductors within the lead body of ventricular lead 18. Electrodes 34, 36 and 38 can be used for both cardiac pacing and sensing of ventricular depolarizations, often referred to as ventricular events or R-waves. At the proximal end of ventricular lead 18 is a bifurcated connector 42 that is inserted into a connector block 32, and carries three electrical connectors, each coupled to one of the coiled conductors.

A coronary sinus lead 14 includes an elongated insulative lead body carrying one coiled conductor coupled to an elongated coiled defibrillation electrode 46. Electrode 46, illustrated in broken outline, is located within the coronary sinus and great vein of the heart. In some embodiments, however, lead 14 may be located within the left ventricle and configured similarly to lead 18, i.e., as a ventricular lead with ring and tip electrodes for delivery of pacing pulses. At the proximal end of lead 14 is a connector plug 50 that is inserted into carrier block 32, and carries an electrical connector, coupled to the coiled conductor.

In the illustrated embodiment, IMD 10 also includes electrodes 54A and 54B (collectively "electrodes 54") on or within the housing 52 of IMD 10. IMD 10 may include any number of electrodes 54, which may, for example, be used for capture detection or far-field ECG detection. Electrodes 54 may also function as a subcutaneous defibrillation and/or cardioversion electrodes for defibrillation and/or cardioversion of either the atria or ventricles.

IMD 10 may be exposed to non-physiological signals, such as electro-magnetic interference (EMI) or pacing polarization artifacts, which can induce large voltages on one or more of electrodes 22, 24, 26, 34, 36, 38, 46 and/or 54. In the presence of EMI, an analog-to-digital converter (ADC) (not shown in FIG. 2) of IMD 10 may be become overloaded, thereby causing the ADC to output incorrect data that has a number of errors. IMD 10 may analyze the incorrect output data and erroneously interpret the data as indicating a condition that does not exist or fail to indicate a condition that does exist. This may cause IMD 10 to incorrectly apply or disable therapy.

To avoid these situations, IMD 10 may include an overload detection module, an overload prediction module or both that determines whether the ADC of IMD 10 is in or approaching an overload condition due to EMI. When overload prediction module determines that ADC is approaching the overload condition, the ADC may generate an overload warning signal that causes the ADC to be reprogrammed to operate in a high slew mode as described in detail below. When the overload detection module determines the ADC is the overload condition for a particular period of time, the ADC may send an indication to a processor that processes the output of the ADC indicating that the ADC is in or is close to being overloaded. In response to the indication from the ADC, the processor of IMD 10 may disregard, e.g., not analyze, the output of the ADC until receiving an indication that the ADC is no longer in an overloaded state. In some embodiments, IMD 10 may additionally change a mode of operation from demand pacing to reversion pacing.

Figure 3:
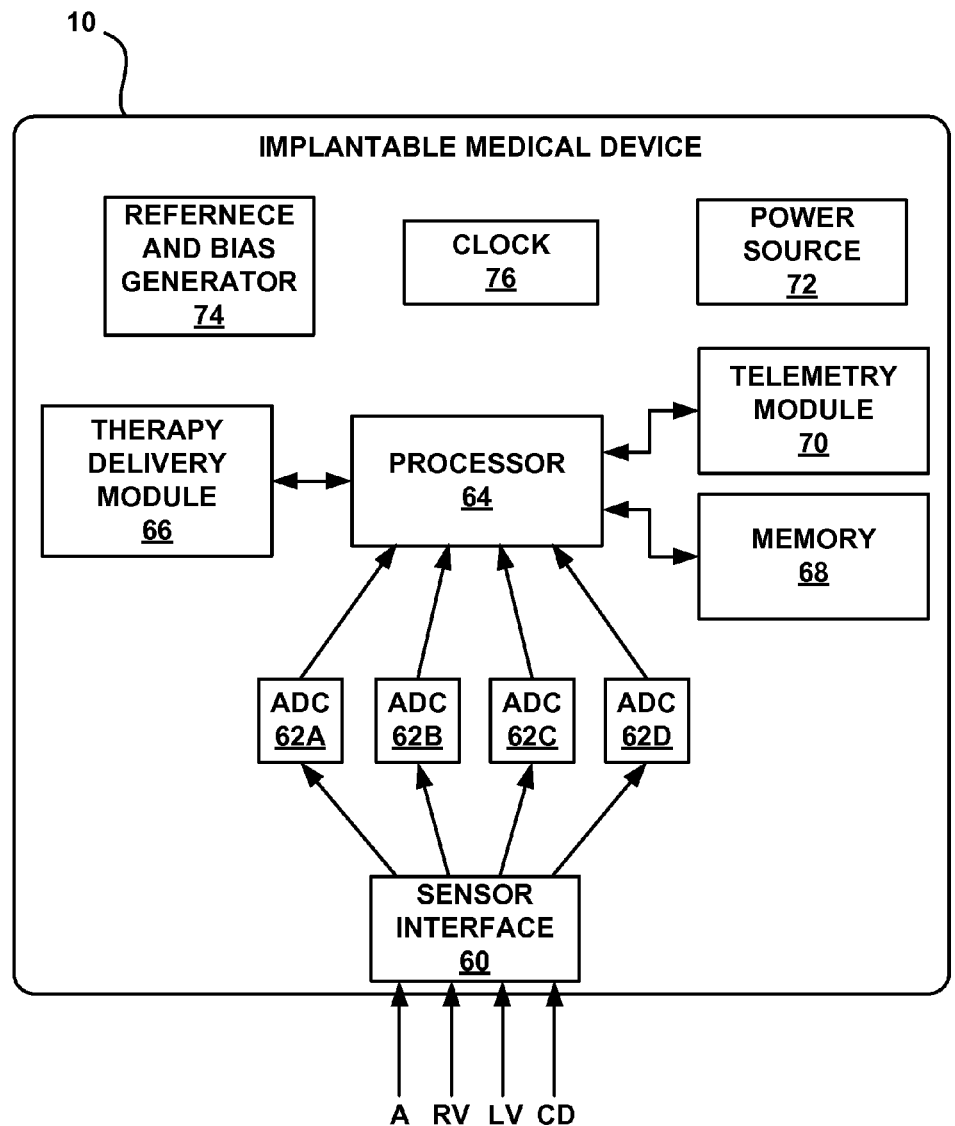
FIG. 3 is a functional block diagram of an IMD.

FIG. 3 is a functional block diagram further illustrating IMD 10. In the example illustrated in FIG. 3, IMD 10 includes a sensor interface 60, ADCs 62A-62D (collectively, "ADCs 62"), a processor 64, a therapy delivery module 66, a memory 68, a telemetry module 70, a power source 72, a reference and bias generator 74 and a clock 76. In the example illustrated in FIG. 3, IMD 10 is a cardiac pacemaker-cardioverter-defibrillator that provides pacing pulses for causing depolarization of cardiac tissue, as well as cardioversion and/or defibrillation pulses, or high-rate pacing, for terminating arrhythmias. Alternatively, IMD 10 may provide other therapies, or be dedicated to sensing, i.e., patient monitoring. In either case, IMD 10 makes use of sensed signals received from one or more sensors via sensor interface 60.

IMD 10 receives signals from one or more sensors and controls delivery of the pacing pulses based on the received signals. Sensor interface 60 of IMD 10 couples to the one or more sensors for receiving the sensed signals. For example, sensor interface 60 may couple to electrodes of one or more leads, such as electrodes 22, 24, 26, 34, 36, 38 and/or 46 of leads 14, 16 and 18 (FIG. 2). In this manner, sensor interface 60 may couple IMD 10 to one or more sensors located outside of IMD 10. Sensors located outside of IMD 10 may be coupled to IMD 10 via leads, or wirelessly coupled to IMD 10. Additionally or alternatively, sensor interface 60 may couple to sensors located on or within a housing of IMD 10. For example, sensor interface 60 may couple to electrodes 54 located on or within the housing of IMD 10 (FIG. 2).

In the example illustrated in FIG. 3, sensor interface receives sensed signals on four channels from electrodes 22, 24, 26, 34, 36, 38 and/or 46 of leads 14, 16 and 18 and electrodes 54 on or within housing 52. In particular, sensor interface 60 receives sensed signals from one or more electrode located in the atrium of a heart of a patient (labeled 'A'), one or more electrodes located in the right ventricle of the heart (labeled 'RV'), one or more electrodes located within the left ventricle of the heart (labeled 'LV'), and one or more electrodes that provide capture detection (labeled 'CD'). The electrodes that provide capture detection may be a different electrode vector of one or more of the electrodes of leads 14, 16, 18. Although IMD 10 is described as receiving sensed cardiac signals, sensor interface 60 may couple to any type of sensor or combination of sensors. For example, sensor interface 60 may be coupled to a pressure sensor, an accelerometer, an activity sensor, an impedance sensor, a temperature sensor, an acidity sensor, or the like. In addition to physiological parameters, sensor interface 60 may couple sensors that monitor parameters other than physiological parameters, e.g., ambient conditions such as pressure or temperature.

Sensor interface 60 provides each of the received signals to a respective one of ADCs 62, which convert the received signal to a digital signal that represents the analog signal. Thus, multiple ADCs 62 are available to support multiple sensing channels. As described above, the multiple sensing channels illustrated in FIG. 3 measure physiological information of different locations in the heart. Although in the example illustrated in FIG. 3, each sensing channel corresponds to its own ADC 62, IMD 10 may have more or fewer ADCs. For example, IMD 10 may include two ADCs and multiplex the input signals into the ADCs such that two input channels are converted from analog to digital using a common ADC. Other combinations or configurations of ADCs may be used. In one embodiment, ADCs 62 may comprise a delta-sigma ADC. However, other types of ADCs may be utilized with the techniques described herein.

ADCs 62 provide the digital signal that represents the analog signal to processor 64. Processor 64 may store the digital signals, portions thereof, or values determined based thereon, in memory 68. Processor 64 may include at least one microprocessor, microcontroller, digital signal processor (DSP), application specific integrated circuit (ASIC), field programmable gate array (FPGA), discrete logic circuitry, or a combination of such components. Memory 68 may include any combination of volatile, non-volatile, magnetic, optical, or solid state media, such as read-only memory (ROM), random access memory (RAM), electronically-erasable programmable ROM (EEPROM), flash memory, or the like.

Processor 64 may transmit the signal, or values determined based on the signal, to an external programmer, via wireless telemetry via telemetry module 70. Telemetry module 70 may include a receiver and a transmitter. Processor 64 may control telemetry module 70 to communicate with the external programmer on a continuous basis, at periodic intervals, or upon request from the external programmer. In addition, in some embodiments, telemetry module 70 may support wireless communication with one or more wireless sensors that sense physiological signals and transmit the signals to IMD 10. The information transmitted via telemetry module 70 may be used by a physician to monitor the condition of the patient, or the efficacy of therapy if IMD 10 delivers therapy. Telemetry module 70 may comprise known circuitry for wireless communication according to any of a variety proprietary or non-proprietary local wireless communication standards.

Processor 64 may also control delivery of therapy to the patient by therapy delivery module 66 based on signals received via sensor interface 60. In the illustrated cardiac pacemaker-cardioverter-defibrillator embodiment, therapy delivery module 66 includes pulse generation circuitry, which may include one or more capacitors, regulators, switches and the like for delivery of pulses or substantially continuous signals, such as sinusoidal signals, to selected chambers of heart 11 via selected ones of electrodes 22, 24, 26, 34, 36, 38 and/or 46 of leads 14, 16 and 18 or electrodes 54 on or within housing 52.

For example, processor 64 may control therapy delivery module 66 to deliver one or more pacing pulses based on the absence of an intrinsic pulse in an ECG detected via one of the sensing channels A, RV, or LV. Such demand pacing is one example in which processor 64 controls therapy delivery module 66 to deliver therapy in response to a sensed signal, i.e., provides responsive therapy. As another example, processor 64 may control therapy delivery module 66 to provide one of the above-discussed arrhythmia termination therapies, based on the sensed signals. Processor 64 may, for example, analyze the digital signals to determine whether the patient is experiencing an arrhythmia and control therapy delivery module 66 to deliver one or more defibrillation or cardioversion pulses when an arrhythmia is detected.

As described above, IMD 10 may be exposed to non-physiological signals, such as electro-magnetic interference (EMI), which can induce large voltages on one or more of electrodes 22, 24, 26, 34, 36, 38, 46 and/or 54. These large voltages may overload ADCs 62, thereby causing the output of ADCs 62 to be incorrect. Processor 64 may analyze the incorrect output of ADCs 62 and erroneously interpret the data as indicating a condition that does not exist or fail to indicate a condition that does exist. This may cause processor 64 to incorrectly apply or disable therapy delivery module 66.

To avoid these situations, IMD 10 may include one or more overload detection modules that determine whether ADCs 62 of IMD 10 are in an overload condition due to the interference. When an overload detection module determines that an ADC 62 is in the overload condition for a particular period of time, e.g., over N of M windows, ADC 62 may send an indication to processor 64 indicating that the ADC is in or is close to being overloaded. In response to the indication, processor 64 may not analyze the output of the ADC until receiving an indication that the ADC is no longer in an overloaded state. In other words, processor 64 disregards the output of ADCs 62 when ADCs 62 are overloaded. Additionally, processor 64 may change mode of operation of therapy delivery module 66 from demand pacing to reversion or other type of pacing as a precautionary measure.

Therapy delivery module 66 may be configured to provide unipolar stimulation or bipolar stimulation. Thus, therapy delivery module 66 may deliver pulses via two or more electrodes on one lead (i.e., bipolar stimulation) or via one electrode on a lead and one of housing electrodes 54 of IMD 10 (i.e. unipolar stimulation). Processor 64 may additionally control therapy delivery module 66 to deliver electrical stimulation with different pulse amplitudes, pulse widths, frequencies (i.e., pulse rates), electrode configurations, or the like based on the sensed signals.

Although IMD 10 FIG. 3 is described in the context of delivering electrical pulses to treat cardiac disorders, IMDs according to various embodiments may generate and deliver stimulation energy for treatment of any of a variety disorders, such as deep brain stimulation (DBS) for movement disorders, psychological discords, epilepsy or pain; spinal cord stimulation (SCS) for pain; pelvic stimulation for pelvic pain, incontinence, or sexual dysfunction; gastric stimulation for gastroparesis, obesity or other disorders; or peripheral nerve stimulation for pain. Another example is muscle stimulation, e.g., functional electrical stimulation (FES) to promote muscle movement or prevent atrophy. The description of IMD 10 as providing cardiac stimulation is provided only as an example, and should not be considered limiting of the types of IMDs in which the techniques described herein may be utilized.

Alternatively, or in addition to providing electrical stimulation, IMD 10 may be configured to provide therapy by delivering fluid to the target site through one or more fluid delivery devices. In embodiments in which one or more fluid delivery devices are part of the therapy elements associated with therapy delivery module 66, therapy delivery module 66 may include one or more fluid reservoirs and one or more pump units that pump fluid from the fluid reservoirs to the target site through the fluid delivery devices. The fluid reservoirs may contain a drug or mixture of drugs. The fluid reservoirs may provide access for filling, e.g., by percutaneous injection of fluid via a self-sealing injection port. The fluid delivery devices may comprise, for example, catheters that deliver, i.e., infuse or disperse, drugs from the fluid reservoirs to the same or different target sites. In this case, processor 64 and therapy delivery module 66 may control which drugs are delivered and the dosage of the drugs delivered based on the sensed signals.

Therapy delivery module 66, processor 64, telemetry module 70, memory 68, sensor interface 60 and ADCs 62 may receive operating power from power source 72. Power source 72 may take the form of a small, rechargeable or non-rechargeable battery, or an inductive power interface that transcutaneously receives inductively coupled energy. In the case of a rechargeable battery, power source 72 similarly may include an inductive power interface for transcutaneous transfer of recharge power.

Minimization of power consumption is desirable for embodiments in which power source 72 is non-rechargeable to prolong the useful life of IMD 10. Minimization of power consumption is also desirable for embodiments in which power source 72 is rechargeable to, for example, reduce the frequency of recharging events and thereby increase the convenience of IMD 10 from the perspective of the patient. To this end, each of ADCs 62 may be a delta-sigma ADC that is configured to provide accurate output for low frequency signals, e.g., signals that are smaller than 100 Hz, with low power consumption, or for signals that have frequencies that are significantly smaller than the clocking frequency (e.g., 1 kHz signals while clocking at 16 kHz). Note that for other IMD applications, such as with drug pumps, the practical clocking frequencies may extend upward to several hundred kilohertz, e.g. 1 kHz signal bandwidth with 50 kHz clocking. To do so, ADCs 62 may utilize a quantizer that has a lower resolution than a digital-to-analog converter (DAC) used for negative feedback. In one embodiment, for example, ADCs 62 may utilize a single bit comparator that drives an up-down counter, which then drives an 8-bit DAC feedback. This configuration provides the benefits of higher resolution DAC feedback, i.e., increased precision to allow for lower quantization noise, without having the use high oversampling ratios that result in high power consumption.

Reference and bias generator 74 supplies reference voltages and/or currents to ADCs 62 and any other circuitry of IMD 10 that requires reference voltages and/or currents. Furthermore, reference and bias generator 74 supplies any bias voltages and/or currents to ADCs 62 and any other circuitry of IMD 10 that requires bias voltages and/or currents. Likewise, clock 76 supplies a clock signal to ADCs 62 and any other circuitry of IMD 10 that needs to be clocked.

Figure 4:
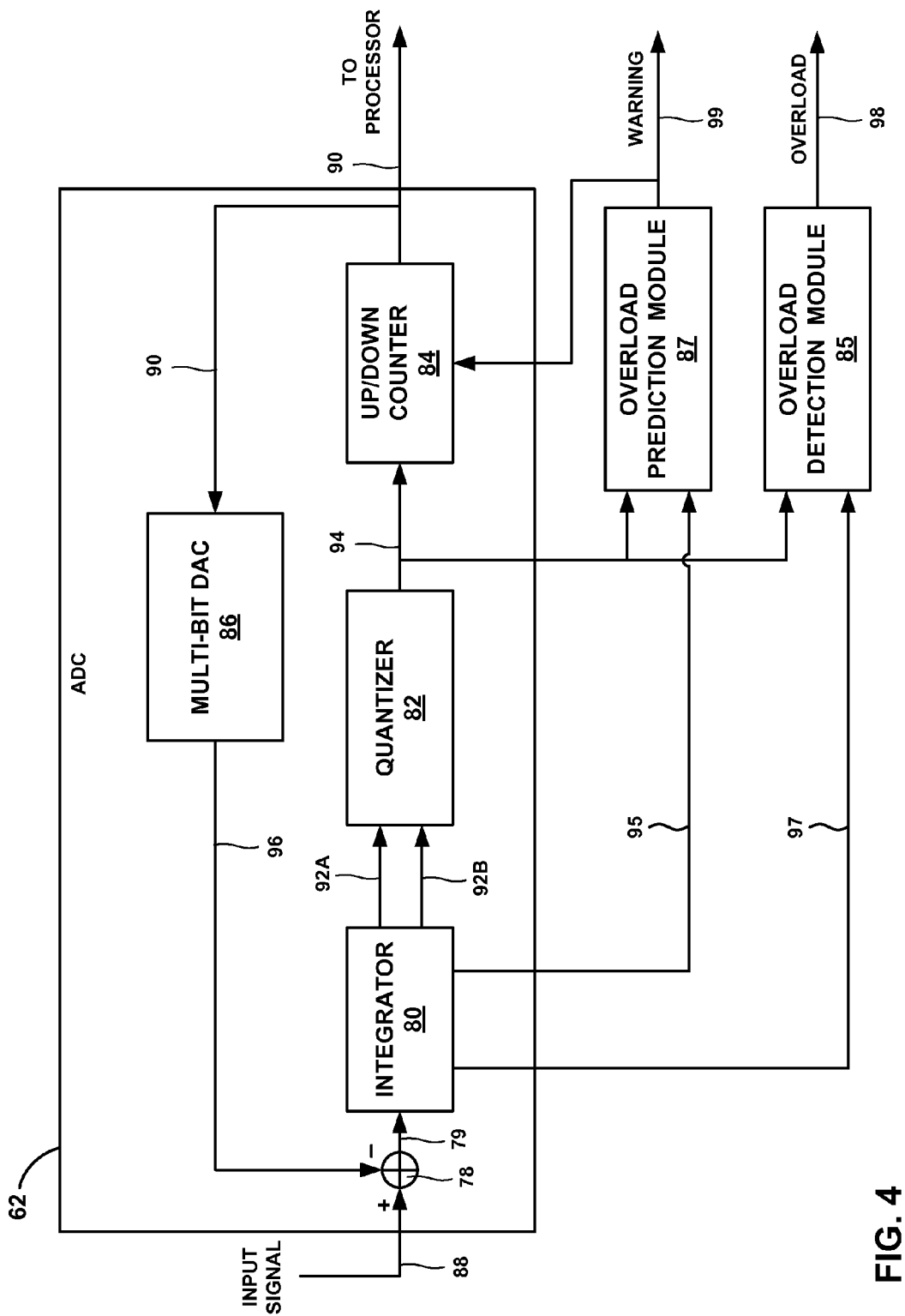
FIG. 4 is a block diagram illustrating an example analog-to-digital converter (ADC) in conjunction with an overload detection module and an overload prediction module.

FIG. 4 is a block diagram illustrating an example ADC 62 in conjunction with an overload detection module 85 and an overload prediction module 87. Overload detection module 85 is configured to detect overloading within ADC 62 in accordance with the techniques described herein. Overload prediction module 87 may predict when ADC 62 is approaching an overload condition and may one or both of output a warning signal to processor 64 or adjust the operation of ADC 62 in response to the prediction. As shown in FIG. 4, ADC 62 includes a difference circuit 78, an integrator 80, a quantizer 82, an up/down counter 84 and a DAC 86 that provides a feedback path. In the embodiment illustrated in FIG. 4, ADC 62 is coupled to overload detection module 85 and overload prediction module 87. Overload detection module 85 and overload prediction module 87 may both be implemented as digital logic circuits separate from ADC 62 or as processes executed by processor 64 of IMD 10. In other embodiments, one or both of overload detection module 85 and overload prediction module 87 may be implemented within ADC 62. In further embodiments, overload detection module 85 and overload prediction module 87 may be implemented as a single digital logic circuit inside or outside of ADC 62 or as a single process executed by processor 64.

ADC 62 operates as a continuous time system. In the example illustrated in FIG. 4, ADC is a continuous time delta-sigma ADC. In the illustrated embodiment, ADC 62 utilizes a differential architecture that includes an integrator that outputs differential signals that are substantially the same in magnitude and substantially opposite in polarity (e.g., 180 degrees out of phase). Other architectures may, however, be used without departing from the scope of this disclosure. In general, ADC 62 is configured to convert a low frequency analog input signal 88 into a digital signal 90. Example low frequency signals include physiological signals and other signals having a frequency of less than approximately 100 Hz. ADC 62 may also be used to accurately convert analog input signals with frequencies that are significantly smaller than a clock frequency used to drive ADC 62. As described above, analog input signal 88 may be obtained from any of a variety of sensors, such as electrodes of one or more leads.

DAC 86 converts digital signal 90 into a reconstructed representation 96 of analog input signal 90, and thereby provides a feedback path for ADC 62. In particular, reconstructed representation 96 is applied to difference circuit 78 as negative feedback. Difference circuit 78 generates a difference signal 79 representative of the difference between input signal 88 and reconstructed signal 96 and provides the difference signal to an input of integrator 80. Integrator 80 integrates the difference signal 79 provided by difference circuit 78. In other words, integrator 80 integrates the difference between input signal 90 and reconstructed representation 96. The integration slope is defined by the voltage to current gain of integrator 80 and an integration capacitor value at integrator 80 outputs.

In the example illustrated in FIG. 4, integrator 80 is a differential integrator. As will be described in more detail in FIG. 5, integrator 80 may include a transconductance amplifier that outputs differential current signals that represent the difference between input signal 90 and reconstructed representation 96. The differential current signals drive capacitive loads that effectively integrate the difference signal 79 to generate differential voltage signals 92A and 92B. Common mode feedback local to the integrator 80 maintains a constant mode voltage at the outputs 92A and 92B. The differential voltage signal 92A and 92B are of an equal magnitude and have opposite polarities, and represent the integrated difference between input signal 88 and reconstructed signal 96. Integrator 80 may have different modes of operation including a normal mode and a clamped mode. When integrator 80 is operating in a normal mode, the integrator outputs 92A, 92B may be indicative of a differential integrated error signal. When integrator 80 is operating in a clamped mode, the integrator outputs 92A, 92B may be indicative of a clamped output signal that is limited by one or both of a positive threshold voltage and a negative threshold voltage. Providing a clamped output signal on differential outputs 92A, 92B of integrator 80 may prevent the DAC feedback loop from being over-driven during start-up or high slew conditions.

Differential integrators provide the advantage of being less affected by any common mode shift in the output voltage. Disturbances at the differential outputs are both shifted by approximately the same amount, thus resulting in little or no change in the difference between the differential outputs. Common mode shifts in the differential output voltages 92A and 92B are rejected by quantizer 82. In other words, noise or other disturbances will affect each of differential signals 92A and 92B equally. Thus, the difference between the two signals is relatively unaffected. Typically, the output difference voltage is small because analog input signal 88 does not experience large signal changes. Consequently, ADC 62 can track changes in analog input signal 88 to produce digital to analog signal 96 as an accurate approximation of input signal 88. In other embodiments, however, integrator 80 need not be a differential integrator.

Quantizer 82 produces a quantization signal 94 that represents a level of the integrated difference between the input signal 88 and the reconstructed signal 96. In the case of a 1-bit quantizer, e.g., a single bit comparator, the output of the comparator is a signal that represents a binary +1 or −1 (or, in some cases either a binary '1' or '0') based on a comparison of the differential signals output by integrator 80. If differential signal 92A is greater than differential signal 92B, which indicates the accumulated error signal is positive signaling that, on average, the integrated input signal 88 is larger than the integrated reconstructed signal 96, the comparator outputs a value of +1. If differential signal 92A is less than differential signal 92B, which indicates the accumulated error signal is negative signaling that, on average, the integrated input signal 88 is smaller than the integrated reconstructed signal 96, the comparator outputs a value of −1, or 0.

In this manner, the 1-bit quantizer determines the sign of the integrated difference, i.e., whether the integrated difference is positive or negative. In other embodiments, quantizer 82 may be a multi-bit quantizer. For example, quantizer 82 may comprise a 2-bit quantizer. In this case, the output of the 2-bit quantizer may represent a +1, 0, or −1 based on the comparison of the differential signals output by integrator 80. In the case of multi-bit quantizers, the quantizer determines not only the sign of the output difference, i.e., whether the output difference is positive or negative, but also the magnitude of the output difference. The higher the resolution of quantizer 82, the more complex quantizer 82 becomes and the more power that is consumed by quantizer 82. If ADC 62 does not operate using a differential architecture, quantizer 82 may produce a quantization signal that represents the level of difference between the output of integrator 80 and a reference voltage.

Quantized signal 94 controls up/down counter 84. In the case of a 1-bit quantizer, quantized signal 94 may be equal to either +1 or −1 (or 0). When quantized signal 94 is equal to +1, quantized signal 94 causes up/down counter 84 to count up. However, when quantized signal is equal to −1 (or 0), quantized signal causes up/down counter 84 to count down. In the case of a multi-bit quantizer, up/down counter 84 may count up and down by larger values or remain at the current count in the case of the quantized signal equaling zero. In this manner, ADC 62 generates digital signal 90 as a digital bit stream that approximates analog input signal 88. The combination of integrator 80 and up/down counter 84 operates as a double integrator and may decrease the stability of the feedback loop of ADC 62. Loop compensation, however, may help to maintain stability of the converter. This compensation can be implemented using analog or digital techniques as described in detail below.

When integrator 80 is in the clamped mode, differential outputs 92A, 92B may be limited by one or both of a positive threshold voltage and a negative threshold voltage, and as a result, may not provide an accurate differential integrated error signal. In other words, when integrator 80 is clamped, differential outputs 92A, 92B may provide a clamped output signal that is smaller than the actual integrated error and therefore, not representative of the accumulated difference between the input signal 90 and reconstructed representation 96. If clamping occurs for a number of consecutive samples or for a large percentage of the consecutive samples, the digital signal 90 output by up/down counter 84 may be significantly inaccurate.

Overload detection module 85 detects whether ADC 62 is in an overload condition that may cause the digital output 90 to be incorrect. In one embodiment, overload detection module 85 may determine whether ADC 62 is in an overload condition based on clamp signal 97 received from integrator 80. In particular, integrator 80 may output a clamp signal 97 indicating that integrator 80 is in the clamping mode, i.e., has experienced a clamp event. Overload detection module 85 may determine that ADC 62 is in an overload condition when a number of time intervals having a clamp event in a contiguous set of time intervals exceeds a programmable threshold. For example, overload detection module 85 may determine ADC 62 is in an overload condition when at least 12 of the last 20 time intervals have experienced a clamp event. Other thresholds or number of time intervals, however, may be used.

Alternatively, or additionally, overload detection module 85 may determine that ADC 62 is in an overload condition based on output 94 of quantizer 82. For a 1-bit quantizer, for example, overload detection module 85 may determine the number of times output 94 of quantizer 82 toggles or switches between +1 and −1 (or 0). During normal operation, output 94 would toggle between +1 and −1 on a frequent basis. Overload detection module 85 may again track a low toggle condition over a number of time intervals to determine that ADC 62 is in an overload condition. Overload detection module 85 may determine that the low toggle condition for a time interval is experienced when a consecutive number of quantizer outputs 94 are in the same direction (e.g., either positive or negative direction). In other words, the low toggle condition is met when there is no toggle in quantizer output 94 for a consecutive number of outputs. Overload detection module 85 may determine ADC 62 is in an overload condition when a number of time intervals during which a low toggle condition is experienced in a contiguous set of time intervals exceeds a programmable threshold. For example, overload detection module 85 may determine ADC 62 is in an overload condition when at least 12 of the last 20 time intervals have experienced a toggle condition.

Overload detection module 85 may output an overload signal 98 to processor 64 (FIG. 2) indicating that ADC 62 is in an overloaded state. In response to overload signal 98, processor 64 disregards the digital signal 90 output by ADC 62. Processor 64 may discard digital signal 90 or may store digital signal 90 in memory, but does not analyze digital signal 90 when ADC 62 is in an overloaded state. When IMD 10 comprises a pacemaker, for example, the processor may disregard intrinsic events within the electrocardiogram while the overload signal 98 from ADC 62 is active. Moreover, IMD 10 may change a mode of operation of the pacemaker from demand pacing to reversion pacing.

Overload prediction module 87 detects when ADC 62 is about to overload and may either output a warning signal to processor 64 or adjust the operation of ADC 62 in response to the prediction. In other words, overload prediction module 87 may detect conditions indicating that ADC 62 is approaching an overload condition and alert processor 64 or reprogram ADC 62 to accommodate for the detected conditions.

In one embodiment, overload prediction module 87 may determine whether ADC 62 is approaching an overload condition based on a clamp warning signal 95 received from integrator 80. In particular, integrator 80 may output a clamp warning signal 95 indicating that integrator 80 is approaching one or both of the positive and negative clamping threshold voltages. Integrator 80 may generate a clamp warning signal when the differential integrated error signal exceeds a certain percentage of either of the clamping threshold voltages. For example, integrator 80 may generate a clamp warning signal when one or both of differential outputs 92A and 92B exceed 75% of the positive clamping threshold.

In some embodiments, overload prediction module 87 may generate an overload warning signal 99 as soon as a clamp warning occurs. Thus, as soon as the first clamp warning occurs, overload prediction module 87 may generate overload warning signal 99. In other embodiments, overload prediction module 87 may generate overload warning signal 99 only after a number of time intervals having a clamp warning in a contiguous set of time intervals exceeds a programmable threshold. For example, overload prediction module 87 may generate an overload warning signal 99 when at least nine of the last twenty time intervals have experienced a clamp warning. Other thresholds or number of time intervals, however, may be used.

Alternatively, or additionally, overload prediction module 87 may determine that ADC 62 is approaching an overload condition based on output 94 of quantizer 82. Overload prediction module 87 may track a low toggle warning over a number of time intervals to determine if ADC 62 is approaching an overload condition. Overload prediction module 87 may determine that a low toggle warning is experienced during a time interval when a consecutive number of quantizer outputs 94 are in the same direction (e.g., either positive or negative). The consecutive number of outputs in the same direction used for determining a low toggle warning may be a percentage of the consecutive number of output in the same direction used for determining a low toggle condition. For example, the consecutive number of outputs in the same direction used for determining a low toggle warning may be 75% of the consecutive number of outputs in the same direction used for determining a low toggle condition.

In some embodiments, overload prediction module 87 may generate an overload warning signal as soon as a low toggle warning occurs. In other embodiments, overload prediction module 87 may generate an overload warning only after a number of time intervals having a low toggle warning in a contiguous set of time intervals exceeds a programmable threshold. For example, overload prediction module 87 may generate an overload warning when at least nine of the last twenty time intervals have experienced a low toggle warning. Other thresholds or number of time intervals, however, may be used.

Overload prediction module 87 may output a warning signal 99 to processor 64 (FIG. 2) indicating that ADC 62 has experienced either a clamp warning or a low toggle warning. In response to warning signal 99, processor 64 may reprogram ADC 62 to operate in a high slew mode in order to accommodate for the increased loading conditions of ADC 62. Switching ADC 62 from a normal mode of operation to a high slew mode of operation may refer to one or both of the following: (1) increasing the magnitude of the increments and decrements for up/down counter 84; or (2) increasing the clocking rate of ADC 62.

For example, processor 64 may reprogram ADC 62 such that up/down counter 84 increments and decrements by a binary value of two (e.g., by +2/−2) as opposed to incrementing or decrementing by a binary value of one (e.g., by +1/−1) as occurs during normal counting mode. Alternatively, warning signal 99 may be sent directly to up/down counter 84 to switch up/down counter 84 to a high slew counting mode. As described above, up/down counter 84 increments and decrements by a larger binary value during the high slew counting mode. In other words, the magnitude of the increments and decrements are increased in the high slew counting mode thereby increasing the slew capability of ADC 62. Although in the example described above the high slew counting mode increments and decrements by a binary value of two, the high slew counting mode may be programmed such that it increments and decrements by other larger binary values, e.g., three, four, five or the like.

In another example, processor 64 may reprogram ADC 62 such that the clocking rate of the feedback loop is increased in response to warning signal 99. For example, when warning signal 99 indicates the existence of high slew conditions in ADC 62, processor 64 may switch the clocking rate of the feedback loop in ADC 62 from 16 kHz to 32 kHz so that up/down counter 84 may increment or decrement twice as many times during a given time interval thereby increasing the slew capability of ADC 62. In other words, the increased clock frequency may linearly increase the slew capability of ADC 62. Alternatively, warning signal 99 may be sent directly to clock 76 (FIG. 3) to increase the clocking rate of ADC 62. Although in this example the increased clocking rate is two times the normal clocking rate of ADC 62, other multiples of the normal clocking rate may be used.

Overload prediction module 87 may also deactivate warning signal 99 indicating that ADC 62 is no longer approaching an overload condition or that a set period of time has elapsed since the issuance of warning signal 99. When warning signal 99 is deactivated, processor 64 may reprogram ADC 62 to operate in a normal slew mode. Switching ADC 62 from a high slew mode of operation to a normal slew mode of operation may refer to one or both of the following: (1) decreasing the magnitude of the increments and decrements for up/down counter 84 (e.g., up/down counter 84 incrementing or decrementing by lower values such as +1 and −1); or (2) decreasing the clocking rate of ADC 62 (e.g. switching ADC 62 from a 32 kHz clocking rate to a 16 kHz clocking rate). In some embodiments, warning signal 99 may be provided directly to up/down counter 84 of ADC 62 to switch up/down counter 84 from a high slew counting mode (e.g., +2/−2) to a normal counting mode (e.g., +1/−1). In other embodiments, warning signal 99 may be provided directly to clock 76 to decrease the clocking rate of ADC 62.

In one embodiment, the overload prediction module 87 may deactivate warning signal 99 based on one or both of clamp warning signal 95 and output 94 of quantizer 82. In such an embodiment, overload prediction module 87 may deactivate warning signal 99 only after an accumulated number of time intervals in a set of contiguous time intervals do not register either a clamp warning or a low toggle warning. In other embodiments, overload prediction module 87 may deactivate warning signal 99 after a set time period has expired, e.g. 1 ms. In this case, overload detection module 87 deactivates warning signal 99 independent of clamp warning signal 95 and the output of quantizer 82.

DAC 86 is a multi-bit DAC that uses digital signal 90 to generate the reconstructed representation of input signal 88, i.e., reconstructed signal 96. As described above, DAC 86 forms a feedback path that applies reconstructed signal 96 as negative feedback to the input of integrator 80. DAC 86 provides continuous feedback in a stable manner to integrate the error between input signal 88 and reconstructed signal 96. In some embodiments, the resolution of DAC may be higher than the resolution of quantizer 82. In one embodiment, for example, quantizer 82 may comprise a single bit comparator that drives an up-down counter, which then drives an 8-bit feedback DAC. The effective resolution of DAC 86 may adjust as up/down counter 84 is reprogrammed. For example, the effective resolution of DAC 86 may be 8 bits when up/down counter 84 is in a normal counting mode and reduce to 7 bits when up/down counter 84 is reprogrammed to operate in a high slew counting mode.

This configuration provides the benefits of higher resolution DAC feedback. The result is increased precision due to lower quantization noise without using high oversampling ratios or higher order loop filtering that consume large amounts of energy. The increased precision may thereby reduce oversensing that could result in providing therapy when it is not needed. For example, the increased precision may reduce oversensing of intrinsic depolarizations in an ECG signal, which could lead to improper delivery of pacing pulses. Additional advantages are discussed in this disclosure or may occur to those skilled in the art upon consideration of this disclosure. Moreover, such advantages may not coexist in every embodiment.

The feedback loop of ADC 62 may have an operating frequency that is higher than the frequency at which the digital signal 90 is output to the processor. In other words, ADC 62 may integrate the error between input signal 88 and reconstructed signal 96 using oversampling. In one embodiment, the feedback loop of ADC 62 may have an operating frequency of 16 kHz or 32 kHz while the frequency at which digital signal 90 is output to the processor may be 1 kHz. In other words, the feedback loop of ADC 62 integrates the error between input signal 88 and reconstructed signal 96 at approximately 16 or 32 times the rate at which the digital signal is output. Nonetheless, the high resolution feedback provided by the multi-bit DAC may further provide the advantage of a lower oversampling ratio, i.e., lower operating frequency of the feedback loop, relative to embodiments with a lower resolution DAC.

ADC 62 may be useful in many different applications. This disclosure presents various example embodiments of ADC 62. However, these example embodiments should not be considered limiting of the ADC 62 as broadly embodied and described in this disclosure. Rather, it should be understood that the example embodiments described in this disclosure are a subset of many different example embodiments within the scope of this disclosure.

Figure 5:
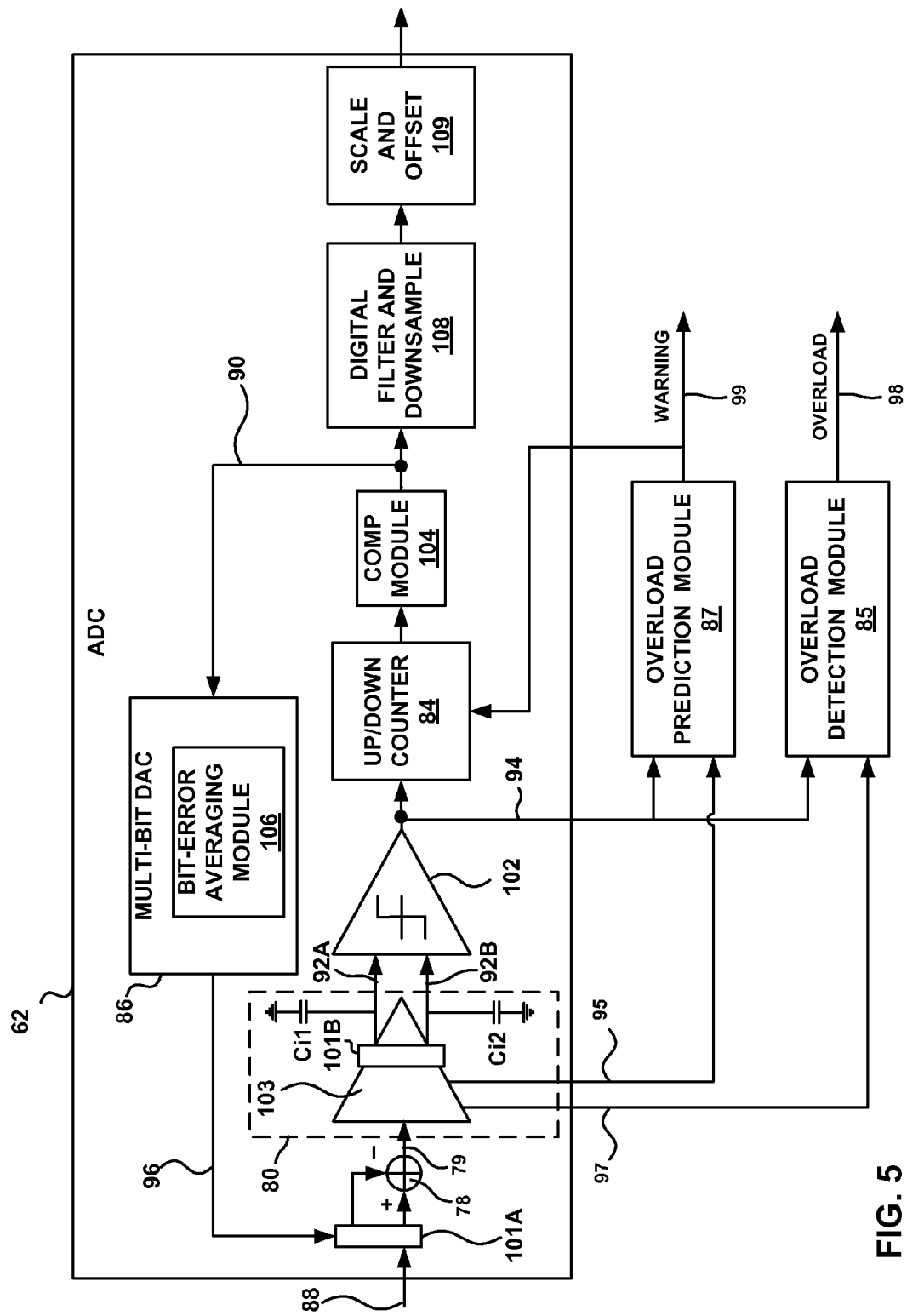
FIG. 5 is a diagram illustrating an example ADC in more detail in conjunction with an overload detection module and an overload prediction module.

FIG. 5 is a diagram illustrating an example delta-sigma ADC 62 in more detail. ADC 62 receives an input signal 88 from a sensor. A chopper module 101A chops input signal 88 and reconstructed signal 96 up to the carrier (chop) frequency prior to application of the input signal to difference circuit 78. The original baseband signal components of input signal 88 and reconstructed signal 96 may have a frequency within a range of 0 to approximately 100 Hz and the carrier frequency may be approximately 4 kHz to approximately 16 kHz. It should be understood, however, that ADC 100 may be used for input signals with other frequency ranges and chop frequencies. For example, ADC 100 may be used in other implementations in which the input signal has a frequency that is significantly less than the clock frequency (e.g., an input signal of 1 kHZ and a clock frequency of 50 kHz). Chopping the inputs to the carrier frequency may allow segregation of the original low frequency components from low frequency noise, e.g., noise from one or more components of ADC 62 or external signals that may enter the signal pathway at a low (baseband) frequency.

The chopped signals are provided to difference circuit 78, which generates a difference signal 79 representative of the difference between input signal 88 and reconstructed signal 96. Difference circuit 78 provides the difference signal to an input of integrator 80. In particular, integrator 80 includes a transconductance amplifier 103, a second chopper module 101B and a pair of capacitors Ci1 and Ci2. Difference signal 79 is amplified by transconductance amplifier 103. Chopper module 101B may modulate the amplified difference signal to upmodulate noise from the amplifier to the carrier frequency and demodulate the original baseband signal components from the carrier frequency back to baseband. In other words, chopper module 101B segregates the noise and the signal of interest. The clock signals driving chopper modules 101A and 101B should be synchronous with each other. In some embodiments, the clock signals driving chopper modules 101A and 101B may be the same signal, i.e., supplied by the same clock. In the example illustrated in FIG. 5, chopper module 101B is located within transconductance amplifier 103, but may be a separate component, e.g., a separate modulator. As described above, the signal output by transconductance amplifier 103 and chopper module 101B is a differential current.

Capacitors Ci1 and Ci2 function as an integrator 80 that converts the differential current into a differential voltage. Moreover, capacitors Ci1 and Ci2 operate on the demodulated signal to pass the low frequency input signal components at baseband and substantially eliminate noise components that are located at the carrier frequency. In this manner, integration may be designed to provide a stable feedback path with acceptable bandwidth while also filtering out the upmodulated random telegraph signal ("RTS") or (popcorn) noise, 1/f noise, and offset from the measurement band. In other words, integrator 80 provides first order filtering of the upmodulated noise. One method of compensating the sigma delta feedback loop is to add a pole zero resistor capacitor network to integrator 80 outputs 92A and 92B. In other embodiments, compensation may be provided by other circuitry. However, the use of integrator 80 as described in this disclosure may be desirable to reduce power consumption. In one embodiment, integrator 80 may comprise a continuous time fully differential Gm/C integrator. The Gm/C integrator may be useful because it consumes relatively little power. Moreover, Gm/C integrators are generally limited by input differential range (i.e., the difference from DAC to input) of about 150 mV, thereby providing a linear circuit over a limited differential range. A high resolution DAC is helpful in that it helps limit the difference signal applied to the integrator. In other embodiments, however, integrator 80 may comprise a different type of differential integrator or a non-differential integrator.

Integrator 80 outputs differential voltage signals 92A and 92B that represent the integrated voltage difference between input signal 88 and reconstructed feedback 96. Differential signals have an equal magnitude and opposite polarities. Integrator 80 may have different modes of operation including a normal mode and a clamped mode. When integrator 80 is operating in a normal mode, the integrator outputs 92A, 92B may be indicative of a differential integrated error signal. When integrator 80 is operating in a clamped mode, the integrator outputs 92A, 92B may be indicative of a clamped output signal that is limited by one or both of a positive threshold voltage and a negative threshold voltage on differential outputs 92A, 92B of integrator 80.

The differential outputs 92A and 92B of integrator 80 are input to a comparator 102. Comparator 102 samples differential signals 92A and 92B to resolve the sign of the integrator output. The sign of the integrator output, i.e., whether 92A is greater than 92B or 92B is greater than 92A, indicates whether the accumulated (integrated) error signal is positive or negative.

In one embodiment, comparator 102 may be a differentially strobed comparator. For example, comparator 102 may be strobed at an operating frequency of 16 kHz or 32 kHz. Thus, comparator may sample differential signals 92A and 92B at a sampling frequency of 16 or 32 kHz. In this manner, comparator 102 functions as a single bit quantizer. In other embodiments, however, a multi-bit quantizer that has a lower resolution than multi-bit DAC 86 may be used.

Up/down counter 84 is driven by the output 94 of comparator 102 such that up/down counter 84 is incremented and decremented according to the sign of the integrator output level. In particular, up/down counter 84 is incremented when the sign of the integrator output level is positive, i.e., the accumulated error is positive. On the other hand, up/down counter 84 is decremented when the sign of the integrator output level is negative, i.e., the accumulated error is negative. In one embodiment, up/down counter 84 may be a 9-bit up/down counter with an 8-bit output. This may be due to the slew capability of the overall output response being limited to one DAC value changed per every two clock cycles. Thus, up/down counter 84 may have a programmable mode that will count by either +/−1 (normal counting mode) or +/−2 (high slew counting mode) fore each comparator output at the loop sampling rate. In other words, during "normal" counting mode, counter 84 may need to count up or down two values before the DAC output would change, essentially ignoring the LSB of the counter. During "high slew" counting mode, the 9-bit counter would effectively become an 8-bit counter. The combination of integrator 80 and up/down counter 84 operates as a double integrator and may decrease the stability of the feedback loop in ADC 62.

ADC 62 may, however, be made more stable by inserting a digital zero or a pole-zero pair into the transfer function of the feedback loop. To provide closed loop stability, ADC 62 may include a compensation module 104. Compensation module 104 may compensate for the double integrator phase shift in the feedback loop. Compensation module 104 may introduce a zero to the closed loop transfer function. This compensation technique keeps the design modulating in a controlled statespace so that the quantization noise is most efficiently shaped to frequencies above the signal passband. In one embodiment, an output of comparator 102 may bypass up/down counter 84 and be added to the output of up/down counter 84. In another embodiment, compensation module 104 may add filter zero at 1-0.5*z$^{-1}$ or at z=+½. Although illustrated in FIG. 5 as inserting a zero into the feedback transfer function in the digital domain, similar techniques may be used to insert a pole-zero pair into the feedback transfer function in the analog domain, e.g., between integrator 80 and comparator 102 at outputs 92A and 92B.

ADC 62 includes a negative feedback loop that includes multi bit DAC 86. The feedback loop continuously cycles in a stable manner integrating the error between input signal 88 and reconstructed signal 96 output by multi bit DAC 86. The feedback loop drives this integral to zero by cycling the DAC output above and below the input signal. In particular, the feedback loop drives the integration of the error downward towards zero when DAC output 96 is above the input signal 88. Similarly, the feedback loop drive the integration of the error upward towards zero when DAC output 96 is below the input signal 88. Thus, over time the positive and negative DAC feedbacks are forced to balance the integration error (integrated difference) between reconstructed signal 96 and input signal 88.

In one embodiment, multi bit DAC 86 may comprise a charge redistribution DAC (CAPDAC). The CAPDAC includes a plurality of capacitors. In one embodiment, the plurality of capacitors may be arranged in two binary weighted CAPDAC arrays; a most significant bit (MSB) array and a least significant bit (LSB array). The CAPDAC arrays may, for example, be partitioned as a 5-bit capacitor array for the MSB array and a 3-bit capacitor array for the LSB array. The 5-bit MSB capacitor array may, for example, include a bank of 31 capacitors and the 3-bit capacitor array may include a bank of 7 capacitors. The two binary weighted arrays may be connected by one inter-stage capacitor (IS). The D/A output voltage can be ideally calculated as:

$$Vdacout = \frac{Vref}{32C}\left[\sum_{i=0}^{4} biCi + \left(\sum_{i=5}^{7} \frac{(biCi)}{8}\right)\right]$$

where bi (i=0:7) represent the binary digits received from the up/down counter 84 and Ci represent the weighted capacitor values of the respective MSB (i=0:4) capacitor array and LSB (i=5:7) capacitor array. The CAPDAC may be formed in a number of other ways. For example, the CAPDAC may include a number of different split arrays or a different number of bits in each of the arrays. Alternatively, CAPDAC may not be a split array, but instead a purely binary weighted array. The CAPDAC described above is described purely as an example of the kind of CAPDAC that may be used in ADC 100.

To improve linearity, noise and resolution of the feedback of multi-bit DAC 86, and hence the overall linearity, noise and resolution ADC 62, multi-bit DAC 86 may include a bit error averaging (BEA) module 106. BEA module 106 may be particularly useful for the capture detection (CD) channel where differential nonlinearity (DNL) error may be more stringent. BEA module 106 may dynamically select which of the capacitors of the MSB array and LSB array to use to represent the bits. For example, BEA module 106 may dynamically select which of the capacitors of the MSB array and LSB array to use to represent the bits, such that the active time of each capacitor is averaged out over time. In one embodiment, BEA module 106 may reselect different active capacitors with every new DAC value. Alternatively, BEA module 106 may select different active capacitors at a slower rate, e.g., every two or three new DAC values. In this manner, the error introduced by the capacitors, e.g., resulting from physical or performance differences between the capacitors is averaged out over time.

As described above, the output of DAC 86 is a reconstructed representation of input signal 88, and is applied to integrator 80 as negative feedback. DAC 86 provides continuous feedback in a stable manner to integrate the error between input signal 88 and reconstructed signal 96. In some embodiments, the resolution of DAC is higher than the resolution of the quantizer, which, in the example illustrated in FIG. 5 is realized by comparator 102. Thus, in the example illustrated in FIG. 5, the quantizer is a single bit comparator that drives DAC 86, which is a multi-bit DAC (e.g., an 8-bit or 9-bit DAC). In other embodiments, however, the quantizer may be realized by a multi-bit (e.g., 2-bit quantizer) that has a lower resolution than multi-bit DAC 86. As described above, such a configuration provides the benefits of higher resolution DAC feedback.

Digital signal 90 is also output to a processor (e.g., processor 64 of FIG. 3) for use in monitoring a condition of a patient and/or controlling delivery of a therapy to the patient. For example, in the embodiment of IMD 10 illustrated in FIG. 3, the digital signal may be output to processor 64 to determine whether delivery of therapy, such as demand pacing or arrhythmia termination, is necessary. Processor 64 may, for example, analyze the digital signals to determine whether the patient is experiencing an arrhythmia and control therapy delivery module 66 to deliver one or more pulses when an arrhythmia is detected. Accordingly, in exemplary embodiments, processor 64 comprises a DSP.

Before outputting digital signal 90 to the processor, digital filter and downsample module 108 filters and downsamples digital signal 90. This operation increases the effective converter resolution by filtering out the higher frequency quantization noise in the digital data stream. At the same time, module 108 reduces the sample rate of the digital data stream. The structure of digital filter and downsample module 108 may be different depending on the sensed signal for which ADC 62 is used. In the example in which ADC 62 is used to sense atrial and/or ventricular signals, digital filter and downsample module may include (1) a summation filter to average two samples when operating at 32 KHz or a 2× multiplier when operating at 16 KHz, (2) an Infinite Impulse Response (IIR) first order low pass digital filter with corner frequencies of approximately 60 Hz for the atrial channel, and approximately 88 Hz for the left/right ventricle channels; and (3) a SYNC filter summing the signal down to an output sampling rate (e.g., 1 KHz or 256 Hz). Digital filter and downsample module 108 may be slightly different for other sensed signals. For the capture detection (CD) channel, digital filter and downsample module 108 may include a 2nd order IIR filter with 579 Hz bandwidth which combines with a 488 Hz bandwidth of a final output sync filter to give a −3 dB frequency of 399 Hz. Digital filter and downsample module 108 may include a different arrangement of filtering and downsampling techniques than those described above based on the type of signal being sensed and/or the desired output characteristics of the processor. For example, digital filter and downsample module 108 may use Finite Impulse Response (FIR) techniques, e.g., sync^2 filter and decimations followed by two stages of half-pass FIR filter and decimator.

After filtering and downsampling the digital signal 90, scale and offset module 109 produces a two's complement output with standard LSB scaling. The output of scale and offset module 109 is then sent to the processor for monitoring the condition of the patient and/or controlling the delivery of therapy to the patient. In the case of demand pacing, as an example, the processor may analyze the digital signal to identify intrinsic depolarizations, e.g., P-waves or R-waves. The processor may identify the intrinsic depolarizations by, for example, comparing digital signal or a first-order derivative of the digital signal to a threshold value. If an intrinsic depolarization is not identified within a predetermined time period, the processor controls therapy delivery circuitry (FIG. 3) to deliver one or more pacing pulses via electrodes 22, 24, 26, 34, 36, 38 and/or 46.

Additionally, in some embodiments IMD 10 provides capture detection. In such embodiments, processor monitors the ECG received via electrodes 92 on or within the housing of the IMD and the CD channel, illustrated in FIGS. 2 and 3, to detect paced depolarizations of the heart during short interval following delivery of a pacing pulse, which indicates that a delivered pacing pulse "captured" the heart. The processor may detect the paced depolarization by, for example, comparing digital signal or a first-order derivative of the digital signal to a threshold value. If the pacing pulse captured the heart, processor may control therapy delivery module to reduce the amplitude of subsequent pacing pulse. If the pacing pulse failed to capture the heart, processor may control therapy delivery module to increase the amplitude of the pacing pulse. In this manner, processor may maintain the pacing pulse amplitude near a minimal value required to capture the heart, thereby conserving power source 72 (FIG. 3).

Furthermore, in some embodiments, IMD 10 acts as a cardioverter or defibrillator. In such embodiments, processor may detect an arrhythmia based on the frequency of intrinsic depolarizations detected within an ECG using the techniques described above. In response to detecting an arrhythmia, processor may control therapy delivery module 66 to deliver a cardioversion or defibrillation pulse via electrodes 22, 24, 26, 34, 36, 38 and/or 46.

As described above, when integrator 80 is in the clamped mode, differential outputs 92A, 92B may be limited by one or both of a positive threshold voltage and a negative threshold voltage. As a result, differential outputs 92A, 92B of integrator 80 may not provide an accurate integrated error signal. In other words, when integrator 80 is clamped, differential outputs 92A, 92B may provide a clamped output signal that is smaller than the actual integrated error and therefore, not representative of the actual integrated difference between the input signal 88 and reconstructed representation 96. If clamping occurs for a number of consecutive samples or for a large percentage of the consecutive samples, the digital signal 90 output by up/down counter 84 may be significantly inaccurate.

Overload detection module 85 detects whether ADC 62 is in an overload condition that may cause the digital output 90 to be incorrect. In one embodiment, overload detection module 85 may determine whether ADC 62 is in an overload condition based on clamp signal 97 received from integrator 80. In particular, integrator 80 may output a clamp signal 97 indicating that integrator 80 is in the clamping mode, i.e., has experienced a clamp event. Overload detection module 85 may determine that ADC 62 is in an overload condition when a number of time intervals having a clamp event in a contiguous set of time intervals exceed a programmable threshold. For example, overload detection module 85 may determine ADC 62 is in an overload condition when at least 12 of the last 20 time intervals have experienced a clamp event. Other thresholds or number of time intervals, however, may be used. For example, overload detection module 85 may determine ADC 62 is in an overload condition when at least 8 of the last 20 time intervals experienced the clamp event, 10 of the last 20, 4 of the last 10, and the like.

Alternatively, or additionally, overload detection module 85 may determine that ADC 62 is in an overload condition based on output 94 of quantizer 82. For a 1-bit quantizer, for example, overload detection module 85 may determine the number of times output 94 of quantizer 82 toggles or switches between +1 and −1 (or 0). During normal operation, output 94 toggles between +1 and −1 on a frequent basis. As an example, output 94 may toggle between +1 and −1 for about 75% of the comparator outputs. Overload detection module 85 may monitor for a low toggle event over a number of time intervals to determine that ADC 62 is in an overload condition. Overload detection module 85 may determine that a low toggle event is experienced during a time interval when a consecutive number of quantizer outputs 94 are in the same direction (e.g., either positive or negative direction) or take on the same value. In other words, the low toggle event is indicative of a lack of sufficient toggle in quantizer output 94 for a consecutive number of outputs. Overload detection module 85 may determine ADC 62 is in an overload condition when a number of time intervals during which a low toggle event is experienced in a contiguous set of time intervals exceeds a programmable threshold. For example, overload detection module 85 may determine ADC 62 is in an overload condition when at least 12 of the last 20 time intervals have experienced a toggle condition.

Overload prediction module 87 detects when ADC 62 is about to overload and may either output a warning signal to processor 64 or adjust the operation of ADC 62 in response to the prediction. In other words, overload prediction module 87 may detect conditions indicating that ADC 62 is approaching an overload condition and alert processor 64 or reprogram ADC 62 to accommodate for the detected conditions. Overload prediction module 87 operates in the same manner as described above with respect to FIG. 4.

Figure 6:
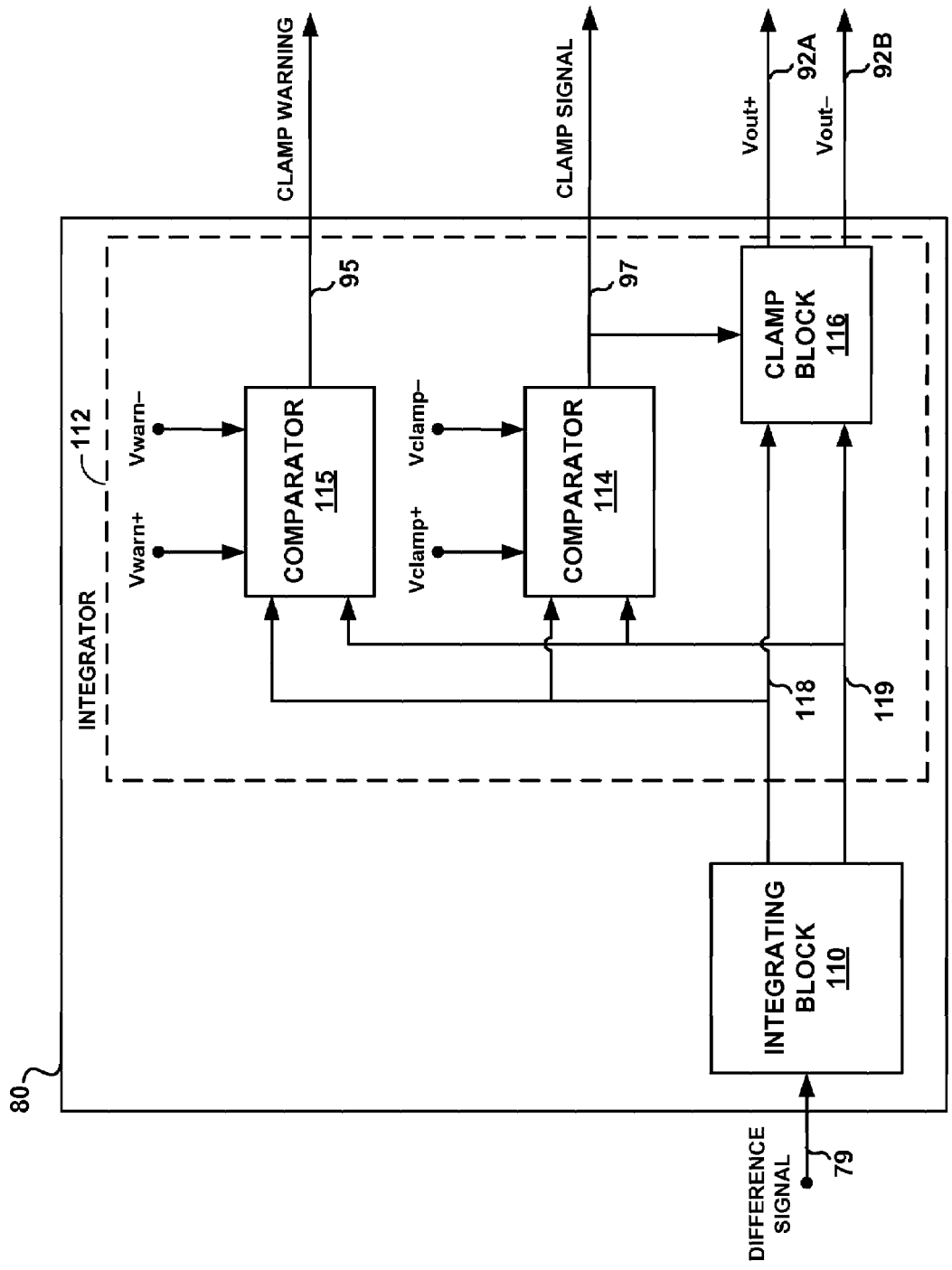
FIG. 6 is a block diagram illustrating an example of an integrator of an ADC in further detail.

FIG. 6 is a block diagram illustrating in further detail an example integrator 80 that may be used in ADC 62. Integrator 80 includes integrating block 110 and integrator clamp module 112. Integrating block 110 may integrate the difference between input signal 88 and reconstructed representation 96 to provide a differential integrated error signal on lines 118 and 119. In the example illustrated in FIG. 6, integrating block 110 is a differential integrator generating a differential integrated error signal on lines 118 and 119. The differential integrated error signal 118, 119 of the integrating block 110 may be fed into integrator clamp module 112.

Integrator clamp module 112 may detect an overload condition in integrating block 110 and adjust the operating mode of integrator 80 in response to whether or not there is an overload condition in the integrating block 110. Integrator clamp module 112 receives a differential integrated error signal represented by lines 118 and 119 and outputs a clamped differential integrated error signal represented by lines 92A and 92B. Integrator clamp module 112 includes comparators 114, 115 and clamp block 116.

Comparator 114 generates a clamp signal 97 indicative of whether integrator is operating in a clamped mode. In particular, comparator 114 detects whether the differential integrated error signal 118, 119 is greater than a positive threshold voltage $V_{clamp+}$, less than a negative threshold voltage $V_{clamp-}$, or both. If the differential integrated error signals 118, 119 is either greater than a positive threshold voltage $V_{clamp+}$ or less than a negative threshold voltage $V_{clamp-}$, comparator 114 activates clamp signal 97 to indicate a clamp event. Conversely, if the differential integrated error signal 118, 119 is less than the positive threshold voltage $V_{clamp+}$ and greater than the negative threshold voltage $V_{clamp-}$, comparator 114 deactivates clamp signal 97. In one embodiment, for example, comparator may output a logic '1' to indicate existence a clamp event (i.e., clamping integrator is operating a clamping mode) or a logic '0' to indicate that there is no clamp event (i.e., clamping integrator is operating a normal mode). In some embodiments, the positive threshold voltage $V_{clamp+}$ and the negative threshold voltage $V_{clamp-}$ may be hardwired into the comparator circuitry or circuit components may be chosen in order to achieve particular positive and negative threshold voltages.

Comparator 114 may also transmit clamp signal 97 to clamp block 116. More specifically, if a clamp condition occurs, comparator 114 may transmit clamp signal 97 to indicate that the integrator 80 is operating in a clamp mode. Conversely, if no clamp condition occurs, comparator 114 may transmit no signal or a signal indicating that integrator 80 is operating in a normal mode. Comparator 114 may transmit information indicating the nature of the clamp condition, e.g., a positive clamp condition or a negative clamp condition, to clamp block 116 instead of or in addition to clamp signal 97.

Comparator 115 generates a clamp warning signal indicative of whether integrator 80 is approaching a clamping condition. The operation of comparator 115 is substantially similar to the operation of comparator 114 except that one or both of the positive and negative threshold voltages may be replaced with warning voltages $V_{warn+}$ and $V_{warn-}$. The warning voltages $V_{warn+}$ and $V_{warn-}$ may be a percentage of the clamping threshold voltages $V_{clamp+}$ and $V_{clamp-}$. For example, $V_{warn+}$ may be about 75% of $V_{clamp+}$ and $V_{warn-}$ may be about 75% of $V_{clamp-}$. Other thresholds may be used. Comparator 115 detects whether the differential integrated error signal 118, 119 is greater than a positive warning voltage $V_{warn+}$, less than a negative warning voltage $V_{warn-}$, or both. If the differential integrated error signals 118, 119 is either greater than a positive warning voltage $V_{warn+}$ or less than a negative warning voltage $V_{warn-}$, comparator 115 activates clamp warning signal 95 to indicate a clamp warning. Conversely, if the differential integrated error signal 118, 119 is less than the positive warning voltage $V_{warn+}$ and greater than the negative warning voltage $V_{warn-}$, comparator 115 deactivates clamp signal 97. In this manner, comparator 115 generates a clamp warning 95 that indicates when integrator 80 is approaching an overload or clamped condition.

Clamp block 116 provides signal conditioning on the differential integrated error signals 118 and 119 to provide a clamped differential integrated error signal on outputs 92A (i.e., $V_{out+}$) and 92B (i.e., $V_{out-}$). If clamp signal 97 from comparator 114 indicates that integrator 80 is operating in a normal mode, clamp block 118 may feed through the differential integrated error signal on lines 118, 119 to outputs 92A, 92B. Otherwise, if clamp signal 97 from comparator 114 indicates that integrator 80 is operating in a clamp mode, clamp block 118 may generate a clamped output signal on outputs 92A, 92B. In one example, the clamped output signal may be limited by one or both of the positive threshold voltage $V_{clamp+}$ and a negative threshold voltage $V_{clamp-}$ on differential outputs 92A, 92B. In another example, the clamped output signal may be any signal with a relatively small voltage difference between lines 92A and 92B so that power consumption is reduced in the DAC loop of the ADC 62.

Figure 7:
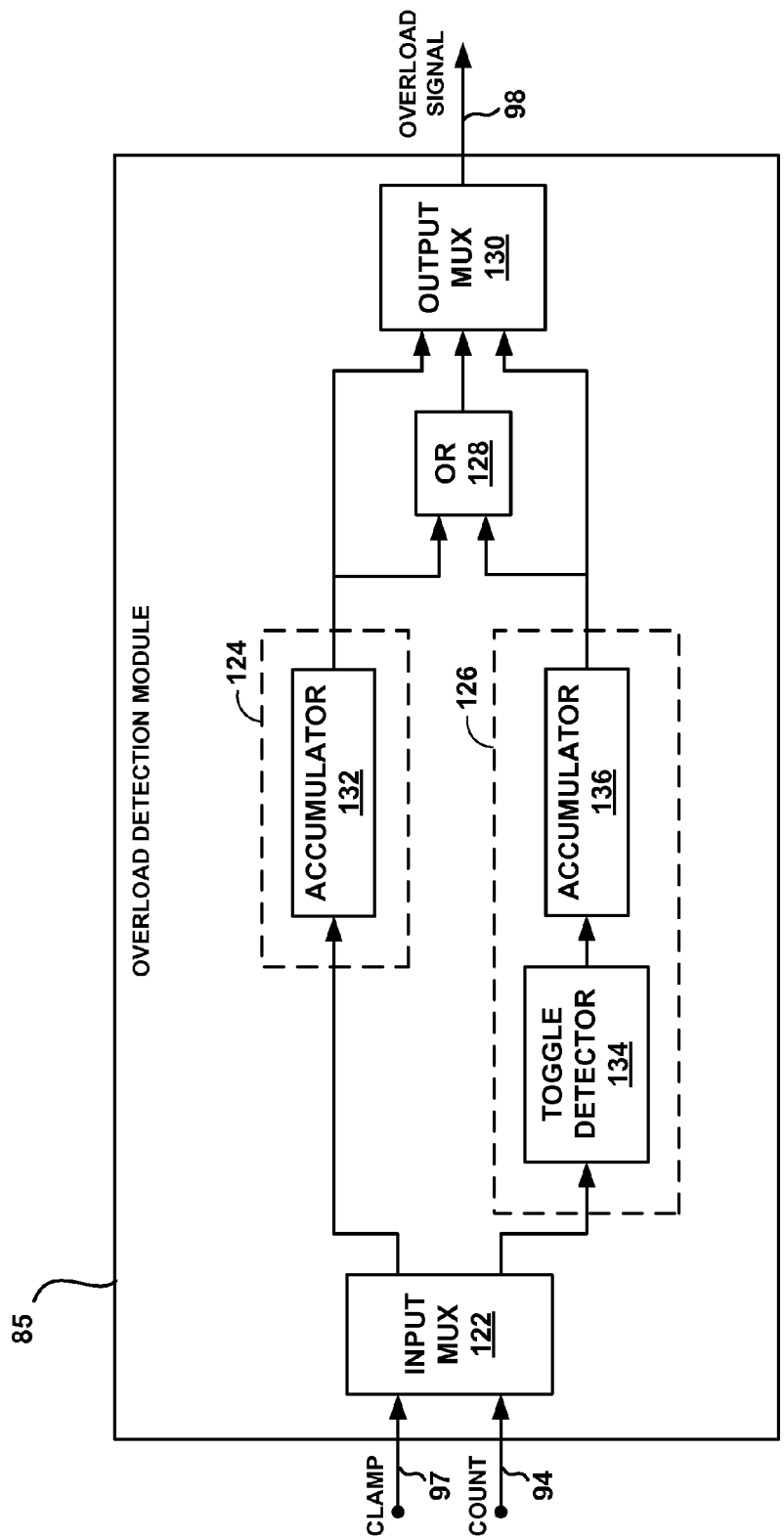
FIG. 7 is a block diagram illustrating an example overload detection module for detecting overload of one or more ADCs.

FIG. 7 is a block diagram illustrating an overload detection module 85 for detecting overload of one or more ADCs, such as ADC 62 of IMD 10. As described above, overload detection module 85 may be embodied as a separate digital logic circuit, as a part of ADC 62 or as a process executed by the processor 64 of IMD 10. In addition, overload detection module 85 may be implemented as a digital circuit or process in combination with overload prediction module 87. Overload detection module 85 determines whether ADC 62 is in an overload condition based on one or more signals received from ADC 62. Upon determining whether ADC 62 is in an overload condition, overload detection module 85 transmits an overload signal 98 to processor 64 indicating ADC 62 is overloaded. Overload detection module 85 includes input multiplexer 122, clamp overload detection module 124, toggle overload detection module 126, "OR" block 128, and output multiplexer 130.

Clamp overload detection module 124 receives clamp signal 97 from ADC 62 and tracks the received clamp signal 97. More specifically, clamp overload detection module 124 may determine the number of time intervals during which a clamp event occurred for a contiguous set of time intervals. In other words, clamp overload detection module 124 may determine the number of time intervals during which clamp signal 97 is activated. For example, clamp overload detection module 124 may include an accumulator 132 that receives clamp events via clamp signal 97 and accumulates the number of time intervals registering a clamp event in a contiguous set of time intervals. If the number of time intervals having a clamp event in the contiguous set of time intervals exceeds a programmable threshold, clamp overload detection module 124 may activate a clamp overload signal 144. Otherwise, if the number of time intervals having during which clamp signal 97 is activated in the contiguous set of time intervals does not exceed a programmable threshold, clamp overload detection module 124 may deactivate the clamp overload signal 144. In this manner, clamp overload detection module 124 may activate overload signal 98 indicating that ADC 62 is overloaded based on clamp signal 97.

Toggle overload detection module 126 may also activate overload signal 98 to indicate that ADC 62 is overloaded. Toggle overload detection module 126 includes toggle detector 134 and an accumulators 36. Toggle detector 134 determines whether a low toggle event is experienced for a particular time interval. As described above, a toggle may comprise transitions from a value of '1' to a value of '−1' or '0', or vice versa. Toggle detector 134 may determine that a low toggle event occurs during a time interval when a consecutive number of quantizer (or comparator) outputs 94 are in the same direction (e.g., either positive or negative direction) or take on a same value for a number of consecutive clock cycles. In other words, the low toggle condition is met when there is not sufficient toggle in output 94 for a consecutive number of outputs.

Accumulator 136 may accumulate the number of time intervals during which a low toggle event occurs. In other words, accumulator 136 determines the number of time intervals during which there is a lack of toggle experienced for the threshold consecutive number of comparator output signals. When accumulator 136 determines that the number of time intervals during which a low toggle event occurs exceeds a programmable threshold, toggle overload detection module 126 may activate overload signal 98. Likewise, if the number of time intervals during which a low toggle event occurs does not exceed the programmable threshold, toggle overload detection module 126 may deactivate overload signal 98.

Overload detection module 85 may detect overload using clamp signal 97 or count signal 94 individually, or a combination of the two. In other words, overload detection module 85 may operate in several modes including: (1) clamp overload detection enabled; (2) toggle overload detection enabled; (3) both toggle overload detection and clamp overload detection enabled; and (4) no overload detection enabled (in which case there is no overload signal output). When only the clamp overload detection is enabled, overload detection module 85 makes the overload detection decision based solely on clamp signal 97. When only the toggle overload detection is enabled, overload detection module 85 makes the overload detection decision based solely on count signal, i.e., the signal from comparator output. Finally, when the overload detection module 85 is operating with both detection mechanisms enabled, overload detection module 85 may determine whether ADC 62 is overloaded based on either clamp signal 97 and the count signal 94. In particular, overload detection module 85 includes an "OR" block 128 that generates a combined overload signal on that is essentially the "or" function of the clamp overload signal and the toggle overload signal. If either clamp overload signal or toggle overload signal are activated, then "or" block activates overload signal 98. Conversely, if the clamp overload signal and the low toggle overload signal are deactivated, then "OR" block 128 deactivates overload signal 98.

Input multiplexer 122 and output multiplexer 130 allow particular input and output signals to pass through based on the mode of operation. For example, input multiplexer 122 may allow only clamp signal 97 to pass through when operating with only the clamp overload detection enabled. Likewise, output multiplexer 130 may route various signals to output signal 98 depending on the mode of operation of overload detection module 85. When the overload detection module 85 is operating in the "both disabled" mode, output multiplexer 130 deactivates output 98. When the overload detection module 85 is operating in the "clamp disabled/toggle enable" mode, output multiplexer 130 routes the clamp overload signal to output 98. When the overload detection module 85 is operating in the "clamp enabled/toggle disabled" mode, output multiplexer 130 routes the toggle overload signal to output 98. Finally, when the overload detection module 85 is operating in the "both enabled" mode, output multiplexer 122 routes combined toggle and clamp overload signal to output 98. In this manner, overload detection module 85 may determine whether analog input signal 88 has exceeded a slew rate limit threshold based on one or both of the clamp signal 97 and the count signal 94.

Figure 8:
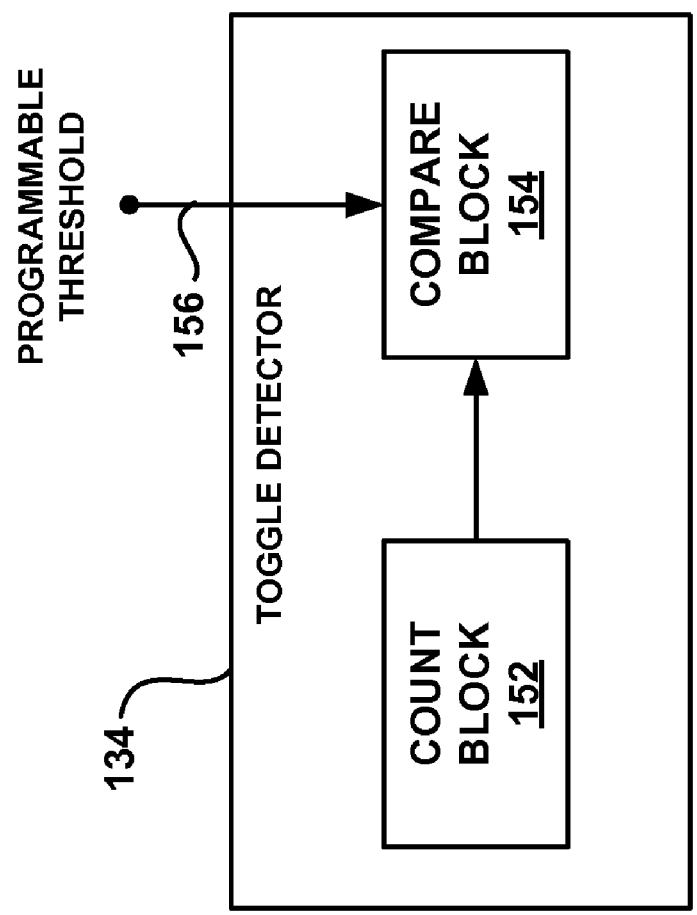
FIG. 8 is a block diagram of an example toggle detector that may be used in an overload detection module or an overload prediction module.

FIG. 8 is a block diagram of an example toggle detector 134, which may be used in the toggle overload detection module 126 of FIG. 7 according to this disclosure. Toggle detector 134 includes count block 152 and compare block 154. Count block 152 counts the total number of consecutive increments or consecutive decrements in a series of consecutive clock cycles. In other words, count block 152 tracks the number of consecutive quantizer outputs with the same sign (i.e., positive or negative outputs). In some cases, count block 152 may track the number of consecutive instances in which the quantizer outputs the same value. If a series of consecutive increments is interrupted with a decrement, count block 152 may reset to a value of one. Likewise, if a series of consecutive decrements is interrupted with an increment, count block 152 may reset to a value of one.

Compare block 154 compares the total number of consecutive increments or consecutive decrements in a series of clock cycles with a programmable threshold to determine if a low toggle event has occurred. If the total number of consecutive increments or consecutive decrements in a series of clock cycles exceeds the programmable threshold 156, compare block 154 may activate low toggle signal to indicate a low toggle event. Likewise, if the total number of consecutive increments or consecutive decrements in a series of clock cycles does not exceed the programmable threshold 156, compare block 154 may deactivate low toggle signal. The programmable threshold input 156 determines the minimum number of consecutive increments or consecutive decrements needed to register a low toggle event. In one example, the programmable threshold may be one of 11, 12, 13, or 14 consecutive counts per 1 ms time interval when the feedback loop of ADC 62 is operating at a frequency of 16 kHz. Compare block 154 may be constructed from any digital or analog comparator known in the art.

Figure 9:
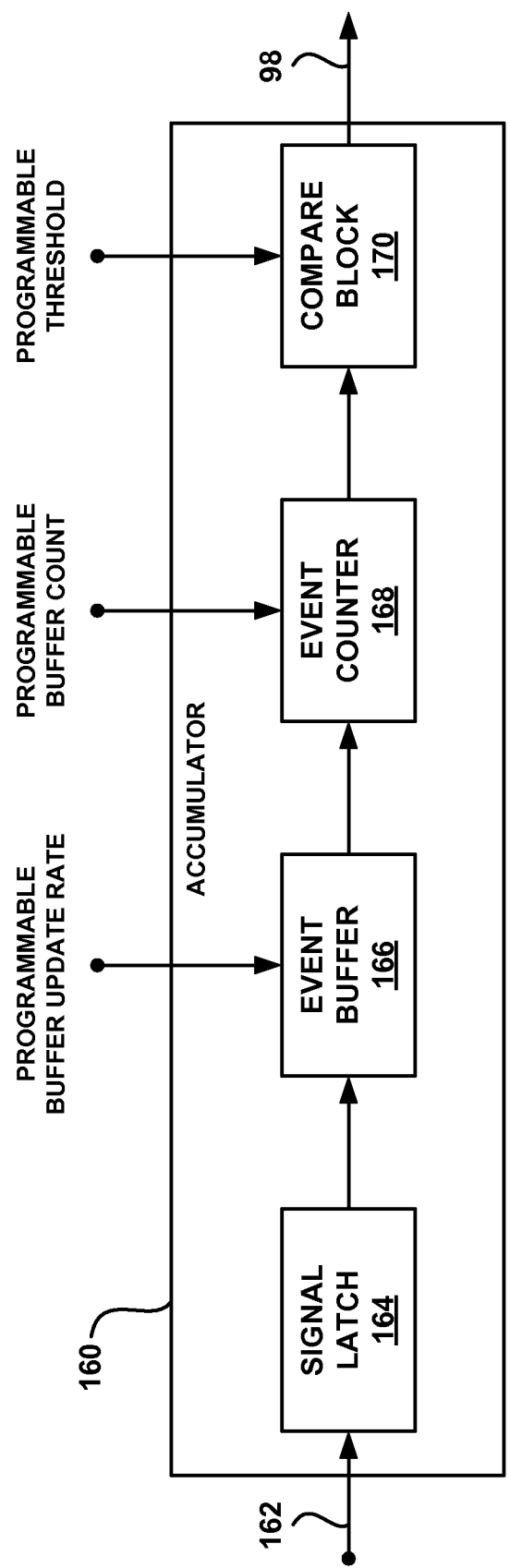
FIG. 9 is a block diagram illustrating an example accumulator that may be used in an overload detection module.

FIG. 9 is a block diagram illustrating an accumulator 160, which may be used in overload detection module 85 of FIG. 7 according to this disclosure. Accumulator 160 may be used in both clamp overload detection module 124 and toggle overload detection module 126 of overload detection module 85 to count the time intervals in a set of contiguous time intervals that register an event. An event may include a clamp event indicating that integrator 80 is operating in a clamped mode or a low toggle event indicating that a low toggle condition has occurred. Accumulator 160 includes signal latch 164, event buffer 166, event counter 168, and compare block 170. Accumulator 160 may receive a programmable buffer update rate input, programmable buffer count input and a programmable threshold input. One or more of these programmable inputs may be adjusted automatically by processor 64 in IMD 10 or by a user via telemetry module 70 in order to customize operation of the overload detection module 85 for particular applications and power requirements.

Signal latch 164 detects an event occurring on event signal 162 during each time interval in a contiguous set of time intervals. Event signal may, for example, be count signal 94 or clamp signal 97. If signal latch 164 detects the occurrence of an event via event signal 162 during a particular time interval, signal latch 162 sends a set buffer signal to event buffer 166 to register the occurrence of an event for that time interval. If signal latch 164 does not detect the occurrence of any events via event signal 162 during a particular time interval, signal latch 164 sends a reset buffer signal to event buffer 166 on to register the non-occurrence of an event for that time interval. Signal latch 164 may be constructed from a latch, flip-flop, or other sequential circuit element that stores state information. The sequential circuit element may be reset at the beginning of each time interval and set during the time interval if an event is detected.

Event buffer 166 stores information indicating whether an event occurred for each time interval in a contiguous set of time intervals. If event buffer 166 receives a set buffer signal from signal latch 164 during a particular time interval, event buffer 166 sets a state element associated with that particular time interval in event buffer 166 to a first state indicating the occurrence of an event during that time interval. If event buffer 166 does not receive a set buffer signal during a particular time interval, event buffer 166 resets the state element associated with that particular time interval to indicate the non-occurrence of an event during that particular time interval.

At the end of a time interval, event buffer 166 may advance the set of contiguous time intervals forward by allocating storage space to include a state element for at least one new time interval. Event buffer 166 may allocate storage space for the at least one new time interval by de-allocating storage space for at least one old time interval. The old time interval may be the oldest time interval in the event buffer. In this manner, event buffer 166 acts as a storage device of event information for a rolling set of contiguous windows. Event buffer 166 may output all of the state information stored in event buffer 166 or some subset thereof on to event counter 168 as described herein. In one example, event buffer 166 may be constructed using a shift register. In other examples, event buffer 166 may be constructed from other sequential elements capable of storing state information for a rolling series of contiguous time intervals.

The length of the time interval may be controlled by a programmable buffer update rate. In one example, the programmable buffer update rate input may switch between a first state that directs the event buffer 166 to update every 5 ms and a second state that directs the event buffer to update every 10 ms. In another example, the programmable buffer update rate input may direct event buffer 166 to update every 1 ms. The programmable buffer update rate may correspond to the clocking rate of event buffer 166. When the programmable buffer update rate is 1 ms, the event buffer 166 provides outputs at the same rate as ADC 60.

Event counter 168 counts the time intervals in a set of contiguous time intervals that have registered events. In particular, event counter 168 may count the number of state elements in event buffer 166 that have been set to indicate the occurrence of an event. In other embodiments, event counter 168 may only count a portion of the state elements in event buffer 166 depending on the programmable buffer count input. Event counter 168 outputs the total number of time intervals in a set of contiguous time intervals that have registered events to compare block 170. In one example, event counter 168 may be constructed from an encoder having one input for each of the state elements in event buffer 166 and outputting a binary output indicative of the total number of state elements that have registered an event. In another example, event counter 168 may be constructed from a counter that increments when an event is initially recorded in event buffer 166 and decrements when a time interval registering an event is de-allocated from event buffer 166.

The number of time intervals in the contiguous set of time intervals may be controlled by a programmable buffer count input. In one example, the programmable buffer count input may be programmed to 20 time intervals such that the number of time intervals in the contiguous set of time intervals is 20. Other numbers of time intervals may be used, however. The contiguous set of time intervals may be referred to as an overall detection window and the individual time intervals may be referred to as sub-windows. In other words, the programmable buffer input controls how many sub-windows are within an overall detection window.

In one example, event counter 168 may use the programmable buffer count input to determine how many state elements of event buffer 166 to include in the total count produced by event counter 168. For example, event buffer 166 may contain more state elements than there are time intervals in the set of contiguous time intervals. If this is the case, event counter 404 may only count a portion of the state elements corresponding to the time intervals within the set of contiguous time intervals.

Compare block 170 compares the total number of time intervals in a set of contiguous time intervals that have registered events with a programmable threshold to determine if an overload condition has occurred. If the total number of time intervals in a set of contiguous time intervals that have registered events exceeds the programmable threshold, compare block 170 may activate overload signal 98. Likewise, if the total number of time intervals in a set of contiguous time intervals that have registered events does not exceed the programmable threshold, compare block 170 may deactivate overload signal 98. The programmable threshold input determines the minimum number of windows that need to register an event in order to detect an overload condition. Compare block 170 may be constructed from any digital or analog comparator known in the art.

Figure 10:
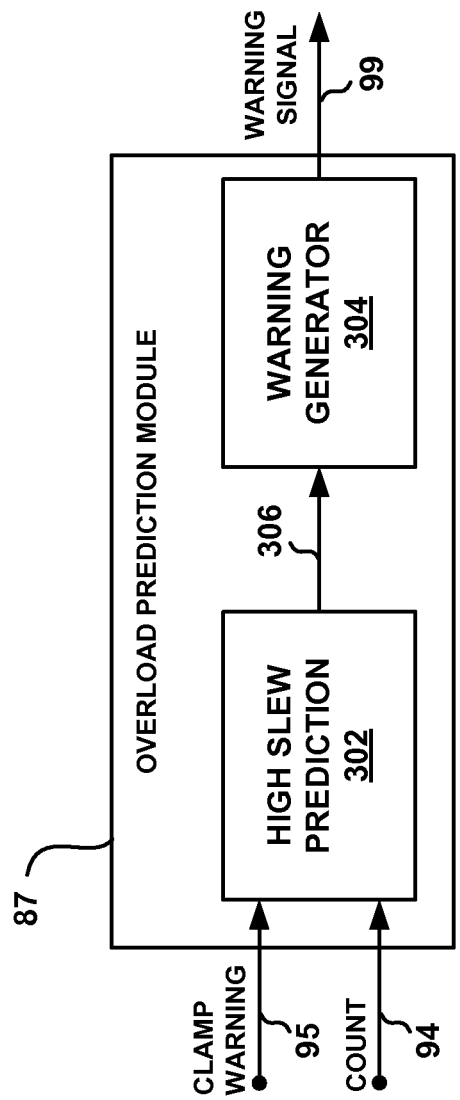
FIG. 10 is a block diagram illustrating an example overload prediction module for detecting when one or more ADCs are approaching an overload condition.

FIG. 10 is a block diagram illustrating an example overload prediction module 87 for detecting when one or more ADCs, such as ADC 62 of IMD 10, are approaching an overload condition. As discussed above, overload prediction module 87 may be embodied as a separate digital logic circuit, as a part of ADC 62 or as a process executed by the processor 64 of IMD 10. In addition, overload prediction module 87 may be implemented as a digital circuit or process in combination with overload detection module 85.

Overload prediction module 87 determines whether ADC 62 is approaching an overload condition based on one or more signals received from ADC 62. Overload prediction module 87 includes high slew prediction module 302 and warning generator 304. High slew prediction module 302 receives a clamp warning signal 95 and/or a count signal 94 and generates a high slew signal 306 based on the received signals from ADC 62. In particular, high slew prediction module 302 may activate high slew signal 306 to indicate a warning condition if either a clamp warning occurs or if a low toggle warning occurs. When there is no clamp warning or no low toggle warning, high slew prediction module 302 may deactivate high slew signal 306. High slew prediction module 302 may update high slew signal 306 simultaneously with the occurrence or non-occurrence of clamp warnings and low toggle warnings in ADC 62. That is, high slew prediction module 302 may activate or deactivate high slew signal 306 several times during a single time interval. In this manner high slew prediction module 87 may track when ADC 62 is approaching an overload condition and when ADC 62 is no longer approaching an overload condition.

Warning generator 304 generates a warning signal 99 that represents a stabilized or debounced version of high slew signal 306. Warning signal 99 may indicate whether ADC 62 should be programmed to operate in a normal mode or a high slew mode. For example, if high slew signal 306 transitions to from a binary "0" to a binary "1," indicating that a clamp warning occurs or if a low toggle warning occurs, warning generator 304 may immediately output a binary "1" on output 99 to indicate that ADC 62 is approaching an overload condition. When high slew signal 306 transitions from a binary "1" back to a binary "0," i.e., no clamp warning or low toggle warning occurs, warning generator may latch the binary "1" on output 99 for a time interval, such as 1 ms. After 1 ms, if high slew signal 306 has remained deactivated (binary "0"), warning generator 304 may revert warning signal 99 back to a binary "0" indicating that ADC 62 is not longer approaching the overload condition. In this manner, warning generator 304 may debounce high slew signal 306 to generate a stabilized warning signal 99. A stabilized warning signal can help prevent rapid switching of ADC 62 between normal and high slew modes. Warning generator 304 may be constructed from a monostable multivibrotor, i.e. a "one shot" circuit, which may hold warning signal 306 in an active state, i.e., a warning condition, for a specific amount of time following the deactivation of high slew signal 316.

Overload prediction module 87 may transmit warning signal 99 to one or both of processor 64 and up/down counter 84. If processor 64 receives the warning signal 99, processor 64 may reprogram ADC 62 to operate in a high slew mode to accommodate for the increased load in ADC 62. If up/down counter 84 receives warning signal 99, up/down counter 84 may switch from a normal counting mode to a high slew counting mode to accommodate for the high slew conditions of input signal 88. In one example, when up/down counter 84 receives warning signal 99, up/down counter 84 may switch from counting by +/−1 (normal counting mode) to counting by +/−2 (high slew counting mode). Likewise, when warning signal 99 is deactivated, up/down counter 84 may revert back from counting by +/−2 to counting by +1/−1. In this manner, ADC 62 may operate in a high slew mode to compensate for an input signal having higher slew rates and to help avoid or delay an overload condition from occurring. This allows ADC 62 to better track the input signal.

Figure 11:
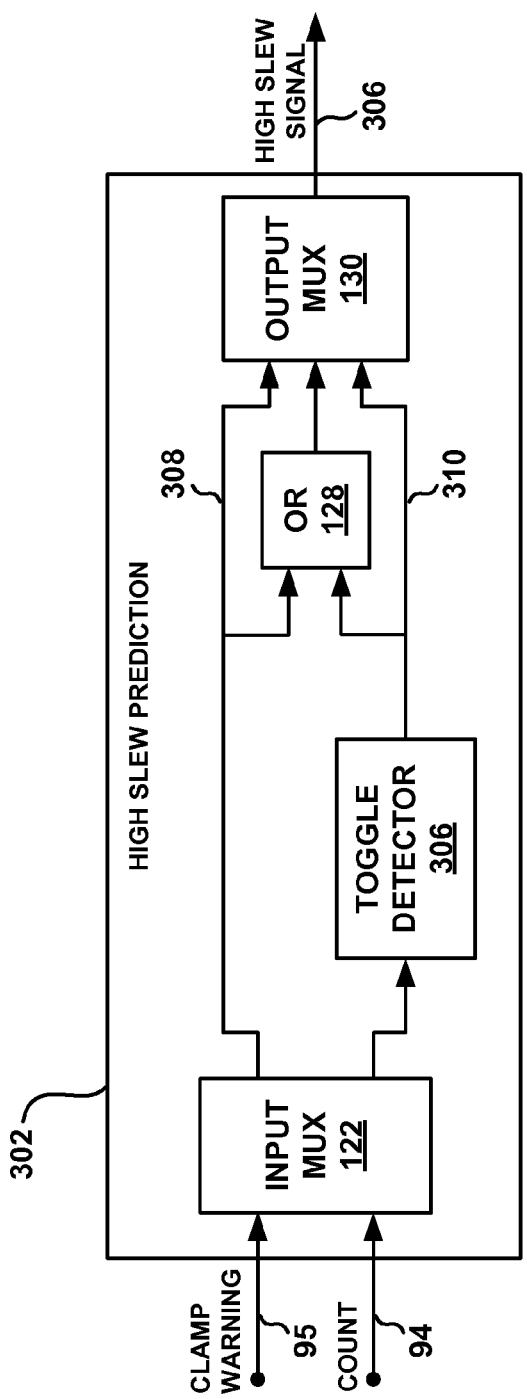
FIG. 11 is a block diagram of an example high slew prediction module that may be used in an overload prediction module.

FIG. 11 is a block diagram of a high slew prediction module 302, which may be used in overload prediction module 87 of FIG. 10. High slew prediction module 302 generates a high slew signal 306 based on one or both of the clamp warning signal 95 and output 94 of quantizer 92 in ADC 62. High slew prediction module 302 includes input multiplexer 122, "OR" block 128, output multiplexer 130, and toggle detector 306.

Input multiplexer 122, "OR" block 128, and output multiplexer 130 multiplex the inputs and outputs of high slew prediction module 302 depending on the mode of operation of the overload prediction module 87. Similar to overload detection module 85, overload prediction module 87 may have different operating modes depending on whether overload prediction is based on the clamp warning signal 97, the output 94 of quantizer 82, or both. Because input multiplexer 122, "OR" block 128, and output multiplexer 130 are substantially similar in structure and operation to the identically numbered components illustrated in overload detection module 85 of FIG. 7, these components will not be described in further detail with respect to this Figure.

Toggle detector 306 generates a low toggle warning signal 310 and is substantially similar to toggle detector 134 illustrated in FIG. 8, except that the programmable threshold 156 (FIG. 8) may have a different value. The programmable threshold for toggle detector 306 of overload prediction module 87 may be some percentage of the programmable threshold of toggle detector 134 in overload detection module 85. For example, the programmable threshold for toggle detector 306 may be 75% of the programmable threshold of consecutive number of comparator outputs in the same direction for toggle detector 134. Other thresholds may be used, however. Thus, toggle detector 306 may generate a low toggle warning when a consecutive number of quantizer outputs 94 are in the same direction (e.g., either positive or negative direction). In this manner, toggle detector 306 may detect when ADC 62 is approaching an overload condition.

Figure 12:
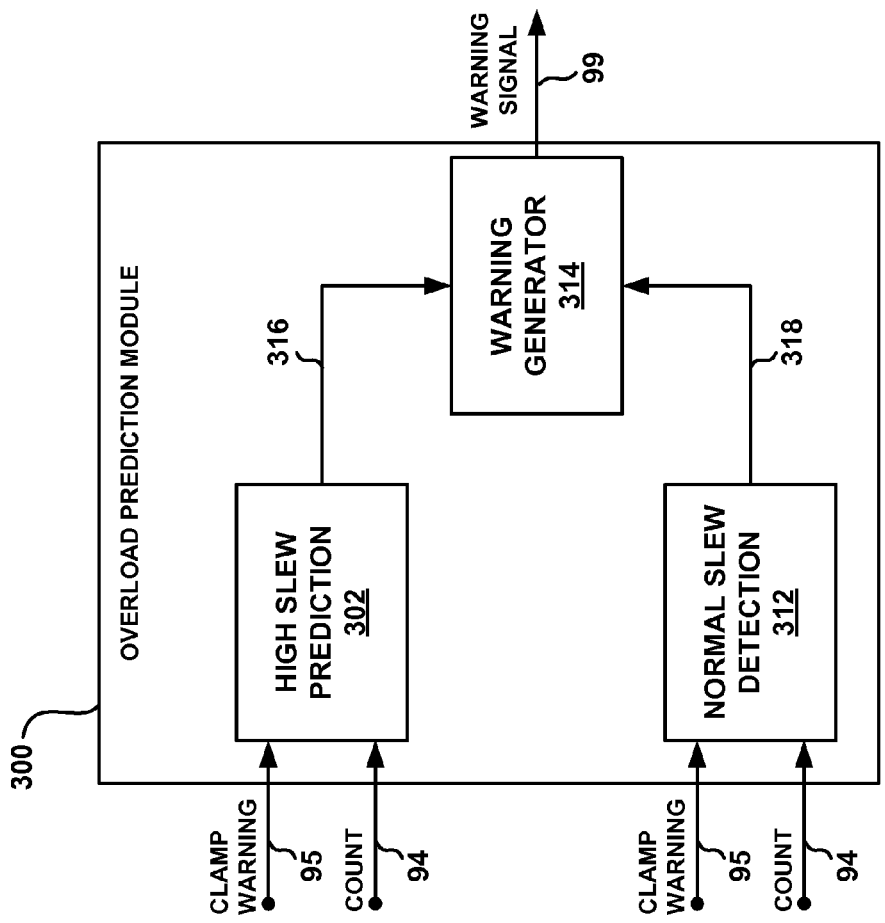
FIG. 12 is a block diagram illustrating another example overload prediction module for detecting when one or more ADCs are approaching an overload condition.

FIG. 12 is a block diagram illustrating another exemplary overload prediction module 300 for detecting when of one or more ADCs, such as ADC 62 of IMD 10, are approaching an overload condition. Overload prediction module 300 includes high slew prediction module 302, normal slew prediction module 312, and warning generator 314. High slew prediction module 302 generates a high slew signal 316 in response to one or both of the clamp warning signal 95 and the output 94 of quantizer 92. The high slew signal 316 indicates that ADC 62 is approaching an overload condition. The operation of high slew prediction module 302 has already been described above with reference to FIGS. 11 and 12 and will not be described in further detail here.

Normal slew detection module 312 generates a normal slew signal 318 in response to both the clamp warning signal 95 and quantizer output 94. Normal slew signal 318 indicates that ADC 62 is no longer approaching an overload condition. In this embodiment, normal slew detection module 312 generates a normal slew signal only after there have been no overload warning conditions for a threshold number of time intervals in a contiguous set of time intervals. In other words, normal slew detection module 312 waits for a condition where there are no clamp warnings and no low toggle warnings for a sufficient number of time intervals to be sure that ADC 62 has actually returned to a normal operating mode.

Warning generator 314 generates a warning signal 99 that represents whether ADC 62 should be programmed to operate in a normal mode or a high slew mode. Warning generator 314 outputs the signal most recently received from inputs 316, 318. For example, if warning generator 314 receives a high slew signal on line 316, warning generator 314 may output a binary "1" to indicate that ADC should be programmed to operate in a high slew mode. Then, warning generator 314 may hold the binary "1" until warning generator 314 receives a normal slew signal on line 318. When warning generator 314 receives a normal slew signal on line 318, warning generator 314 may output a binary "0" to indicate that ADC 62 should be programmed to operate in a normal mode. Warning generator 314 may be constructed from a bistable multivibrator such as an S-R flip-flop.

Figure 13:
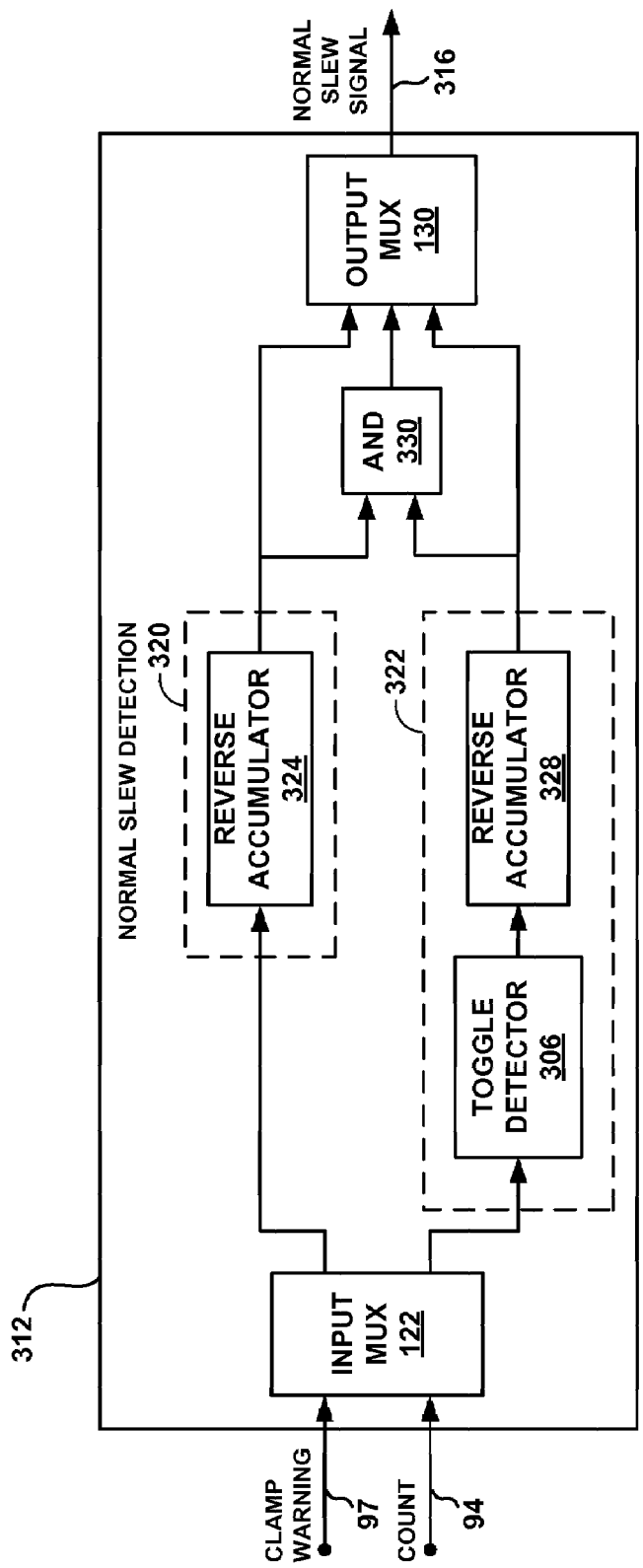
FIG. 13 is a block diagram of a normal slew detection module that may be used in an overload prediction module.

FIG. 13 is a block diagram illustrating a normal slew detection module 312, which may be used in the overload prediction module of FIG. 12. Normal slew detection module 312 provides a normal slew signal 316 indicating that ADC 62 should be programmed to operate in a normal mode. Normal slew detection module 312 includes input multiplexer 122, output multiplexer 130, clamp detection module 320, toggle detection module 322, and "AND" block 330.

Input multiplexer 122, output multiplexer 130 and "AND" block 330 multiplex the inputs and outputs of normal slew detection module 302 depending on the mode of operation of the overload prediction module 87. Similar to overload detection module 85, overload prediction module 87 may have different operating modes depending on whether overload prediction is based on the clamp warning signal 97, the quantizer output 94, or both. Because input multiplexer 122 and output multiplexer 130 are substantially similar in structure and operation to the identically numbered components illustrated in overload detection module 85 of FIG. 7, these components will not be described in further detail here. The "OR" block 128 (FIG. 7) has been replaced by "AND" block 330. In normal slew detection module 312, an "AND" block 330 is used because the normal slew signal 316 should not be activated until both the accumulated clamp warning signal and the accumulated low toggle signal indicate that ADC 62 is no longer approaching an overload condition. "AND" block 330 generates a combined accumulated signal that is essentially the "and" function of the accumulated clamp signal and the accumulated toggle signal. The output of "AND" block 330 is activated only when the accumulated clamp signal and the accumulated toggle signal both indicate that ADC is no longer approaching an overload condition. If either the accumulated clamp signal or the accumulated toggle signal indicate that ADC is approaching an overload condition, "AND" block 330 deactivates the output.

Clamp detection module 320 outputs an accumulated clamp detection signal to output multiplexer 130 and "AND" block 330. The accumulated clamp detection signal is activated when the clamp warning signal is deactivated, i.e. indicates no clamp warning, for a threshold number of time intervals in a contiguous set of time intervals. Clamp detection module 320 includes reverse accumulator 324. Reverse accumulator 324 is substantially similar to accumulator 160 (FIG. 9) except that compare block 170 activates signal 98 when the output of event counter 168 is less than a programmable threshold. Also, the programmable threshold used in clamp detection module 320 may be different than the programmable threshold used in clamp overload detection module 124 in overload detection module 85 (FIG. 7). Clamp detection module 320 uses a reverse accumulator so that it may output an accumulated clamp detection signal when the number of time intervals registering a clamp warning in a contiguous set of time intervals is less than a programmable threshold. In other embodiments, clamp detection module 320 may use a standard accumulator 160 (FIG. 6) and invert the clamp warning signal 95 before it is fed into the accumulator.

Toggle detection module 322 outputs an accumulated low toggle signal to output multiplexer 130 and "AND" block 330. The accumulated low toggle signal is activated when there are no low toggle events for a threshold number of time intervals in a contiguous set of time intervals. Toggle detection module 322 includes toggle detector 306 and reverse accumulator 328. Low toggle detector 306 generates a low toggle warning when up/down counter 84 has counted in the same direction for a threshold number of clock cycles. The low toggle warning is fed into reverse accumulator 328. Reverse accumulator 328 counts the number of time intervals in a contiguous set of time intervals that registered low toggle warnings. If the number of time intervals registering low toggle warnings is less than a programmable threshold, then reverse accumulator 328 activates an accumulated toggle signal indicating that ADC 62 is no longer approaching an overload condition. In other embodiments, an accumulator, such as accumulator 160, could be used instead of reverse accumulator 128 if the output of toggle detector 306 is inverted.

Figure 14:
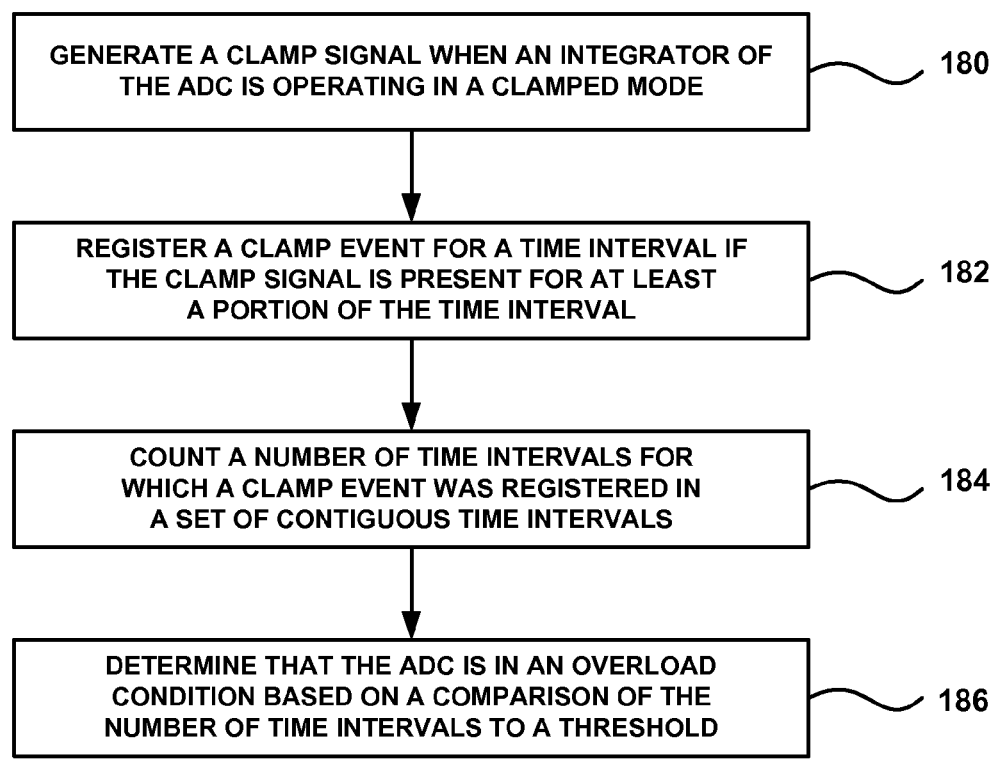
FIG. 14 is a flow diagram illustrating example operation of a clamp overload detection module.

FIG. 14 is a flow diagram illustrating example operation of a clamp overload detection module, such as clamp overload detection module 124 of FIG. 7, designed in accordance with the techniques of this disclosure. Clamping integrator 80 generates a clamp signal when an integrator of the ADC 62 is operating in a clamped mode (180). Clamp overload detection module 124 registers a clamp event for a time interval if the clamp signal is present for at least a portion of the time interval (182). Clamp overload detection module 124 counts a number of time intervals for which a clamp event was registered in a set of contiguous time intervals (184). Clamp overload detection module 124 determines that the ADC 62 is in an overload condition based on a comparison of the number of time intervals to a threshold (186). For example, clamp overload detection module 124 determines that the ADC 62 is in an overload condition when 12 of the last 20 time intervals experienced a clamp event.

Figure 15:
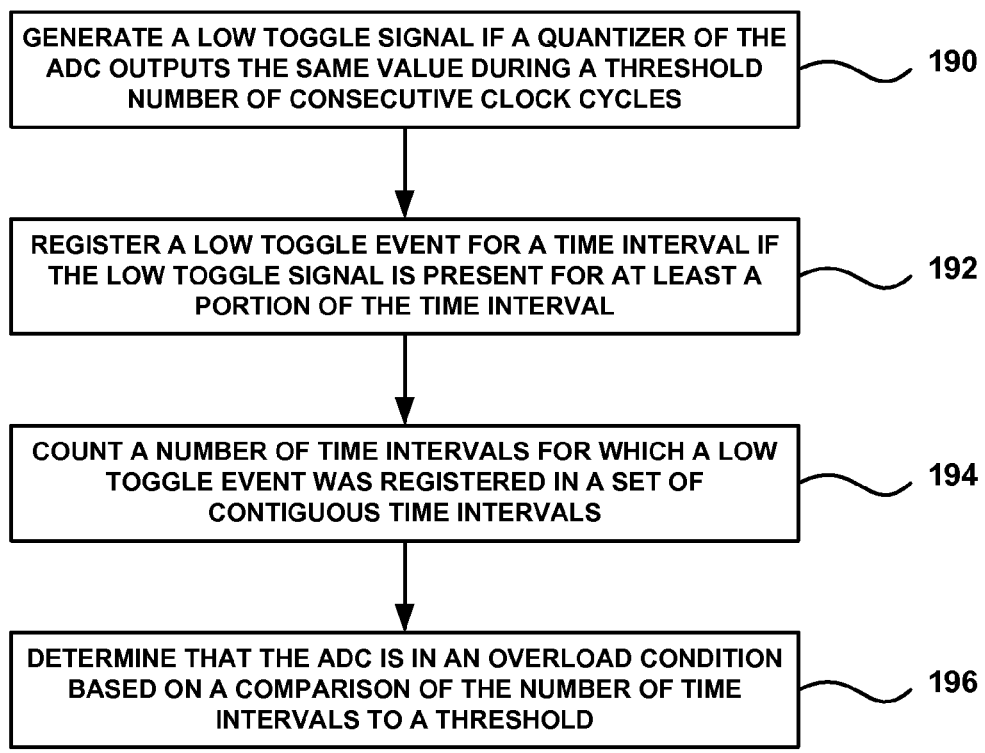
FIG. 15 is a flow diagram illustrating example operation of a toggle overload detection module.

FIG. 15 is a flow diagram illustrating example operation of a toggle overload detection module, such as toggle overload detection module 126 of FIG. 7, designed in accordance with the techniques of this disclosure. Toggle overload detection module 126 generates a low toggle signal if a quantizer of ADC 62 outputs the same value during a threshold number of consecutive clock cycles (190). Toggle overload detection module 126 registers a low toggle event for a time interval if the clamp signal is present for at least a portion of the time interval (192). Toggle overload detection module 126 counts a number of time intervals for which a low toggle event was registered in a set of contiguous time intervals (194). Toggle overload detection module 126 determines that ADC 62 is in an overload condition based on a comparison of the number of time intervals to a threshold (196).

Figure 16:
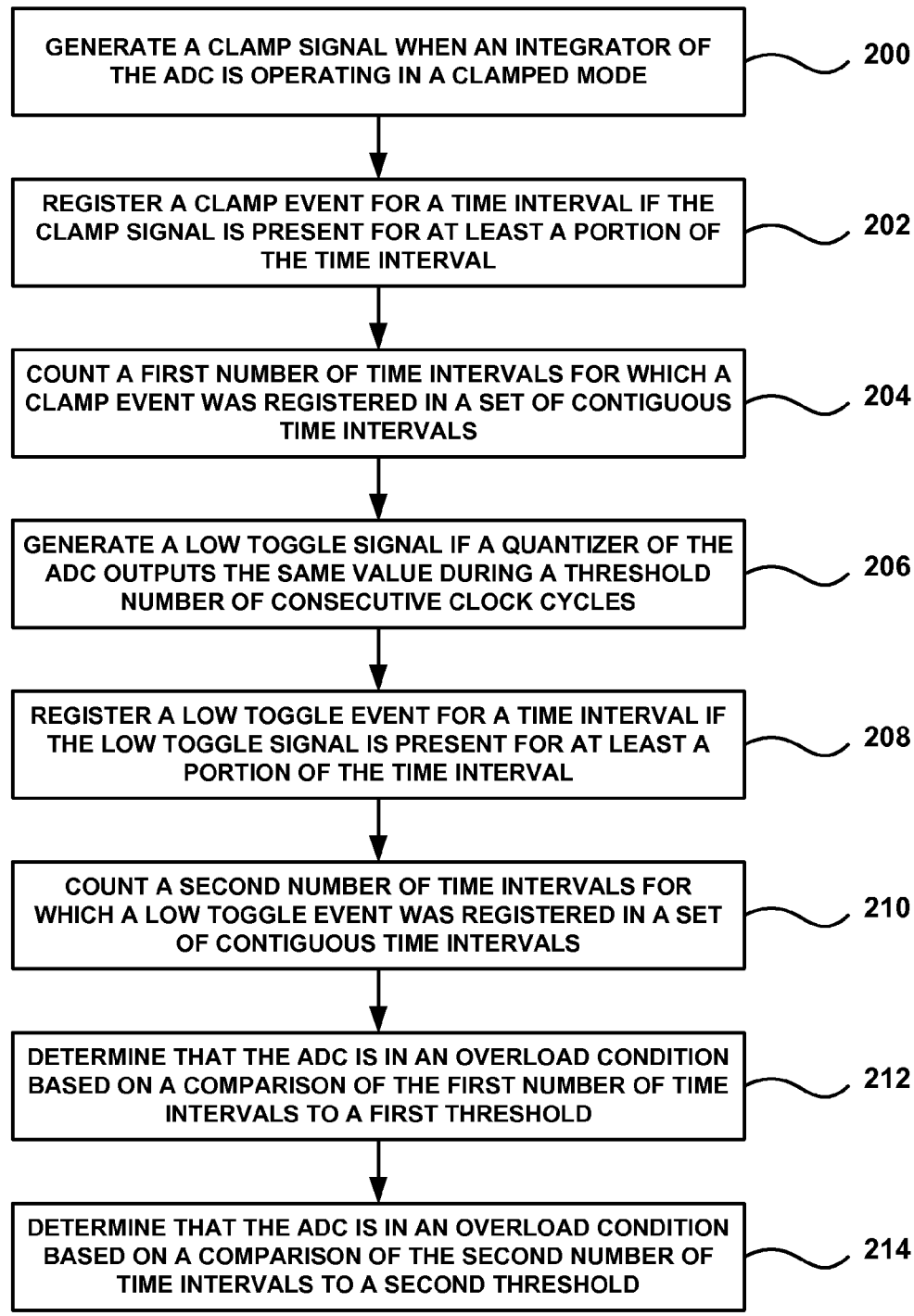
FIG. 16 is a flow diagram illustrating example operation of an overload detection module that includes both toggle overload and clamp overload detection schemes.

FIG. 16 is a flow diagram illustrating example operation of an overload detection module, such as overload detection module 85 of FIG. 7, designed in accordance with the techniques of this disclosure. Clamping integrator 80 generates a clamp signal when an integrator of the ADC is operating in a clamped mode (200). Overload detection module 85 registers a clamp event for a time interval if the clamp signal is present for at least a portion of the time interval (202). Overload detection module 85 counts a first number of time intervals for which a clamp event was registered in a set of contiguous time intervals (204). Overload detection module 85 generates a low toggle signal if a quantizer of the ADC outputs the same value during a threshold number of consecutive clock cycles (206). Overload detection module 85 registers a low toggle event for a time interval if the clamp signal is present for at least a portion of the time interval (208). Overload detection module 85 counts a second number of time intervals for which a low toggle event was registered in a set of contiguous time intervals (210). Overload detection module 85 determines that the ADC is in an overload condition based on a comparison of the first number of time intervals to a first threshold (212). Overload detection module 85 determines that the ADC is in an overload condition based on a comparison of the second number of time intervals to a second threshold (214). In this manner, the overload detection techniques may be used in combination.

Figure 17:
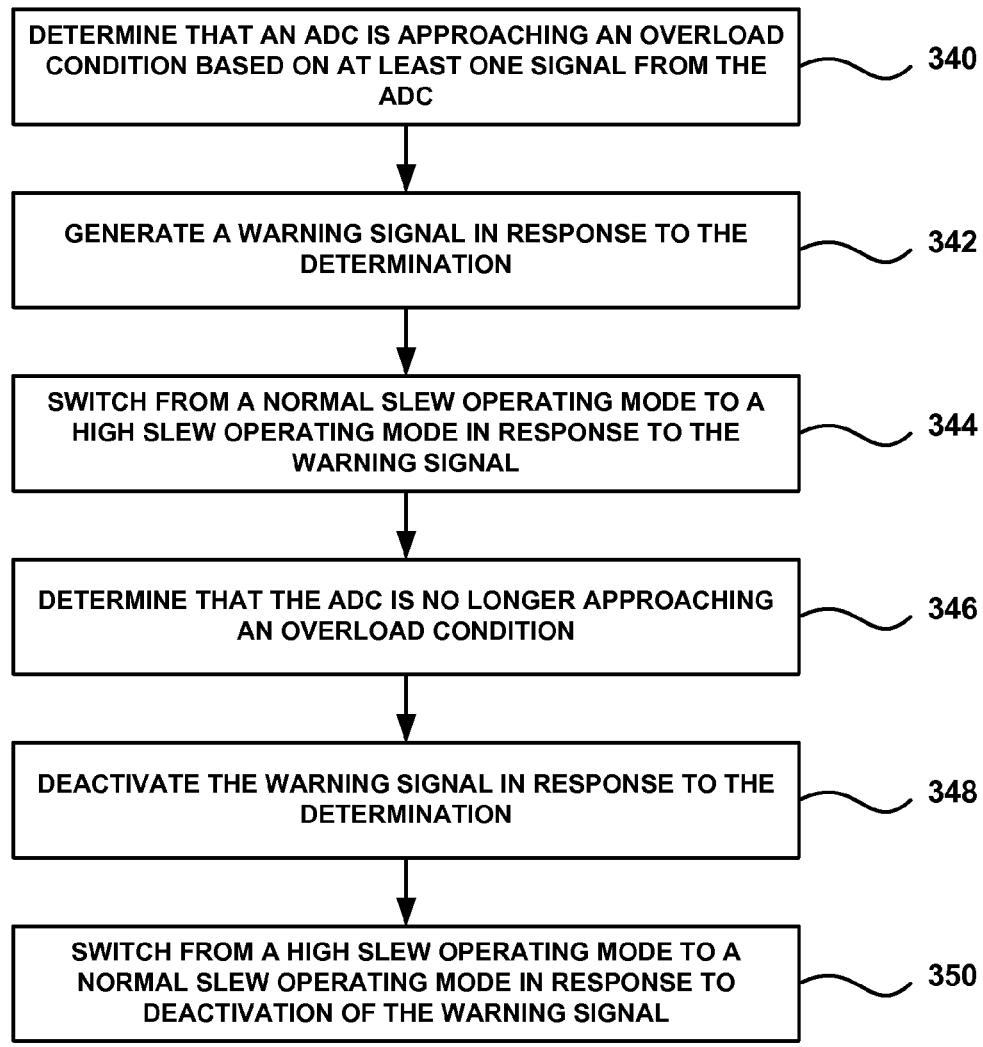
FIG. 17 is a flow diagram illustrating example operation of an ADC in conjunction with an overload prediction module.

FIG. 17 is a flow diagram illustrating example operation of an ADC in conjunction with an overload prediction module, such as ADC 62 and overload prediction module 87 of FIG. 4. Overload prediction module 87 determines that ADC 62 is approaching an overload condition based on at least one signal from ADC 62 (340). Overload prediction module 87 generates a warning signal in response to the determination (342). ADC 62 switches from a normal slew operating mode to a high slew operating mode in response to the warning signal (344). As described in detail above, switching ADC 62 from a normal mode of operation to a high slew mode of operation may refer to one or both of the following: (1) increasing the magnitude of the increments and decrements for up/down counter 84; or (2) increasing the clocking rate of ADC 62. Overload detection module 87 determines that ADC 62 is no longer approaching an overload condition based on the at least one signal from ADC 62 (346). Overload detection module 87 deactivates the warning signal in response to the determination (348). ADC 62 switches from a high slew operating mode to a normal slew operating mode in response to deactivation of the warning signal (350).

Various embodiments of the have been described. However, a person of ordinary skill in the art will recognize that various modifications may be made to the described embodiments without departing from the scope of the claims. For example, although described primarily with reference to a cardiac pacemaker, or pacemaker-cardioverter-defibrillator, the techniques are not so limited. The techniques may be embodied in any implantable medical device, which may deliver any type of therapy, or no therapy.

Furthermore, the techniques are not limited to embodiments in which the therapy is controlled based on the digital signal produced by an ADC according to the techniques. In some embodiments, the signal is merely analyzed for patient monitoring. Additionally, the techniques are not limited to embodiments in which the digital signal is analyzed. In some embodiments, the digital signal produced by an ADC of an IMD according to the techniques are stored with the IMD and/or transmitted to another device, e.g., via telemetry.

Moreover, the techniques are not limited to embodiments in which the analog input signal is an ECG, or even a signal received via electrodes. In other embodiments, an ADC may receive signals from any type of sensor or transducer. As examples, an ADC may receive an EEG; an electromyogram (EMG); a pressure signal, such as intracardiac, intravascular, or intracranial pressure signal; an impedance signal, which may indicate lead functionality, respiration rate, or pulmonary congestion; a temperature signal; a chemical signal such as glucose concentration or pH; an accelerometer signal that indicates patient motion or position relative to gravity; or a sound signal, which may indicate snoring or apnea. Additionally, an ADC may receive non-physiological signals such as ambient temperature or pressure. Such signals may be received from any electrode, transducer, or sensor known to be able to produce a signal that varies as a function of the above-identified physiological and non-physiological parameters. These and other embodiments are within the scope of the following claims.

The invention claimed is:

1. A method of detecting overload in an implantable medical device, comprising:
converting an analog input signal from a sensor into a digital signal with an analog-to-digital converter (ADC) of the implantable medical device;
determining that the ADC is in an overload condition based on at least one signal from the ADC; and
disregarding the digital signal by a processor of the implantable medical device in response to the determination.

2. The method of claim 1, wherein determining that the ADC is in an overload condition based on at least one signal from the ADC comprises:
generating a clamp signal when an integrator of the ADC is operating in a clamped mode; and
determining that the ADC is in the overload condition based on the clamp signal.

3. The method of claim 2, wherein determining that the ADC is in the overload condition based on the clamp signal comprises:
registering a clamp event for a time interval if the clamp signal is present for at least a portion of the time interval;
counting a number of time intervals for which a clamp event was registered in a set of contiguous time intervals; and
determining that the ADC is in the overload condition based on a comparison of the number of time intervals to a threshold.

4. The method of claim 2, wherein determining that the ADC is in an overload condition based on at least one signal from the ADC further comprises:
generating a low toggle signal if a quantizer of the ADC outputs the same value during a threshold number of consecutive clock cycles; and
determining that the ADC is in an overload condition based on both the clamp signal and the low toggle signal.

5. The method of claim 1, wherein determining that the ADC is in an overload condition based on at least one signal from the ADC comprises:
generating a low toggle signal if a quantizer of the ADC outputs the same value during a threshold number of consecutive clock cycles; and
determining that the ADC is in an overload condition based on the low toggle signal.

6. The method of claim 5, further comprising:
registering a low toggle event for a time interval if the low toggle signal is present for at least a portion of the time interval;
counting a number of time intervals for which a low toggle event was registered in a set of contiguous time intervals; and
determining that the analog input signal is in the overload condition based on a comparison of the number of time intervals to a threshold.

7. The method of claim 1, wherein the implantable medical device comprises a cardiac pacemaker, the digital signal comprises an electrocardiogram, and disregarding the digital signal comprises disregarding intrinsic events within the electrocardiogram.

8. The method of claim 7, wherein disregarding intrinsic events within the electrocardiogram comprises changing a mode of operation of the pacemaker from demand pacing to reversion pacing.

9. An implantable medical device, comprising:
an analog-to-digital converter (ADC) that converts an analog input signal from a sensor into a digital signal;
an overload detection module that determines that the ADC is in an overload condition based on at least one signal from the ADC; and
a processor that disregards the digital signal in response to the determination.

10. The implantable medical device of claim 9, wherein:
the ADC further comprises an integrator that generates a clamp signal when the integrator is operating in a clamped mode, and
the overload detection module further comprises a clamp overload detection module that determines that the ADC is in the overload condition based on the clamp signal.

11. The implantable medical device of claim 10, wherein the clamp overload detection module further comprises:
an event buffer that registers a clamp event for a time interval if the clamp signal is present for at least a portion of the time interval;
an event counter that counts a number of time intervals for which a clamp event was registered in a set of contiguous time intervals; and
a compare block that determines that the ADC is in the overload condition based on a comparison of the number of time intervals to a threshold.

12. The implantable medical device of claim 10, wherein overload detection module further comprises:

a toggle overload detection module that generates a low toggle signal if a quantizer of the ADC outputs the same value during a threshold number of consecutive clock cycles;

wherein the overload detection module determines that the ADC is in an overload condition based on both the clamp signal and the low toggle signal.

13. The implantable medical device of claim 9, wherein the overload detection module further comprises a toggle overload detection module that generates a low toggle signal if a quantizer of the ADC outputs the same value during a threshold number of consecutive clock cycles and determines that the ADC is in an overload condition based on the low toggle signal.

14. The implantable medical device of claim 13, wherein the toggle overload detection module further comprises:
an event buffer that registers a low toggle event for a time interval if the low toggle signal is present for at least a portion of the time interval;
an event counter that counts a number of time intervals for which a low toggle event was registered in a set of contiguous time intervals; and
a compare block that determines that the analog input signal is in the overload condition based on a comparison of the number of time intervals to a threshold.

15. The implantable medical device of claim 9, wherein the overload detection module comprises one of a software module implemented by the processor or a digital logic circuit separate from the processor.

16. An implantable medical device, comprising:
an analog-to-digital converter (ADC) that converts an analog input signal from a sensor into a digital signal, wherein the ADC includes a clamping integrator that generates a clamp signal when the clamping integrator is operating in a clamped mode;
an overload detection module that determines that the ADC is in an overload condition based on the clamp signal from the ADC; and
a processor that disregards the digital signal in response to the determination.

17. The implantable medical device of claim 16, wherein the overload detection module further comprises:
an event buffer that registers a clamp event for a time interval if the clamp signal is present for at least a portion of the time interval;
an event counter that counts a number of time intervals for which a clamp event was registered in a set of contiguous time intervals; and
a compare block that determines that the ADC is in the overload condition based on a comparison of the number of time intervals to a threshold.

18. An implantable medical device, comprising:
an analog-to-digital converter (ADC) that converts an analog input signal from a sensor into a digital signal;
an overload detection module that that generates a low toggle signal if a quantizer of the ADC outputs the same value during a threshold number of consecutive clock cycles and determines that the ADC is in an overload condition based on the low toggle; and
a processor that disregards the digital signal in response to the determination.

19. The implantable medical device of claim 18, wherein the processor further comprises:
an event buffer that registers a low toggle event for a time interval if the low toggle signal is present for at least a portion of the time interval;
an event counter that counts a number of time intervals for which a low toggle event was registered in a set of contiguous time intervals; and
a compare block that determines that the analog input signal is in the overload condition based on a comparison of the number of time intervals to a threshold.

20. An implantable medical device comprising:
an analog-to-digital converter (ADC) that converts an analog input signal from a sensor into a digital signal; and
an overload prediction module that determines that the ADC is approaching an overload condition based on at least one signal from the ADC, and generates a warning signal in response to the determination, wherein the ADC switches from a normal slew operating mode to a high slew operating mode in response to the warning signal.

21. The implantable medical device of claim 20, further comprising a counter within the ADC that switches from a normal counting mode to a high slew counting mode in response to the warning signal.

22. The implantable medical device of claim 20, wherein the ADC switches from normal slew operating mode to high slew operating mode by increasing a clocking rate of the ADC.

23. The implantable medical device of claim 20, wherein the overload prediction module determines that the ADC is approaching an overload condition based on one of a clamp warning signal received from an integrator and a low toggle warning signal that indicates a quantizer of the ADC outputs the same value during a threshold number of consecutive clock cycles.

24. The implantable medical device of claim 20, wherein the overload prediction module deactivates the warning signal after a predetermined time period from activation of the warning signal has expired and the ADC switches from the high slew operating mode to the normal slew operating mode in response to deactivation of the warning signal.

25. The implantable medical device of claim 20, wherein the overload prediction module deactivates the warning signal based on the at least one signal from the ADC and the ADC switches from the high slew operating mode to the normal slew operating mode in response to deactivation of the warning signal.

* * * * *